US008067535B2

(12) United States Patent
Terajima et al.

(10) Patent No.: US 8,067,535 B2
(45) Date of Patent: Nov. 29, 2011

(54) IDENTIFICATION OF GENE SEQUENCES AND PROTEINS INVOLVED IN VACCINIA VIRUS DOMINANT T CELL EPITOPES

(75) Inventors: Masanori Terajima, Holden, MA (US); John Cruz, Shrewbury, MA (US); Francis A. Ennis, Shrewsbury, MA (US)

(73) Assignee: The University of Massachusetts, Boston, MA (US)

( * ) Notice: Subject to any disclaimer, the term of this patent is extended or adjusted under 35 U.S.C. 154(b) by 53 days.

(21) Appl. No.: 11/238,122

(22) Filed: Sep. 28, 2005

(65) Prior Publication Data

US 2007/0237790 A1 Oct. 11, 2007

Related U.S. Application Data

(63) Continuation-in-part of application No. 10/764,985, filed on Jan. 26, 2004, now Pat. No. 7,217,526.

(60) Provisional application No. 60/442,846, filed on Jan. 24, 2003.

(51) Int. Cl.
*A61K 38/08* (2006.01)
*A61K 39/285* (2006.01)

(52) U.S. Cl. .................................... 530/328; 424/232.1

(58) Field of Classification Search ............... 424/232.1, 424/93.1; 530/300
See application file for complete search history.

(56) References Cited

U.S. PATENT DOCUMENTS

| | | | | |
|---|---|---|---|---|
| 4,603,112 | A | 7/1986 | Paoletti et al. | |
| 5,674,502 | A | 10/1997 | Ennis | |
| 5,766,601 | A | 6/1998 | Ennis | |
| 5,882,650 | A | 3/1999 | Ennis | |
| 6,232,448 | B1 * | 5/2001 | Yoshikubo et al. | 530/388.26 |
| 6,627,407 | B2 | 9/2003 | Ennis | |
| 6,962,790 | B1 | 11/2005 | Ennis | |
| 7,026,443 | B1 * | 4/2006 | Sette et al. | 530/300 |
| 7,217,526 | B2 | 5/2007 | Terajima et al. | |
| 2004/0132132 | A1 | 7/2004 | Sahin et al. | |
| 2005/0129703 | A1 | 6/2005 | Ennis et al. | |

FOREIGN PATENT DOCUMENTS

| | | | |
|---|---|---|---|
| EP | 1 398 380 | A1 | 3/2004 |
| WO | WO 95/15764 | A1 | 6/1995 |
| WO | WO 95/24925 | A1 | 9/1995 |
| WO | WO 96/03144 | A1 | 2/1996 |
| WO | WO 97/45444 | A1 | 12/1997 |
| WO | WO 98/03192 | A1 | 1/1998 |
| WO | WO 99/02550 | A1 | 1/1999 |
| WO | WO00/24778 | A1 * | 5/2000 |
| WO | WO 02/068682 | A2 | 9/2002 |
| WO | WO 2004/024756 | A2 | 3/2004 |
| WO | WO 2004/067032 | A2 | 8/2004 |
| WO | WO2006/0706003 | A2 * | 7/2006 |

OTHER PUBLICATIONS

Colman P. Research in Immunology, 1994, vol. 145, pp. 33-36.*
Smilek et al. Proc. natl. Acad. Sci. USA, 1991, vol. 88, pp. 9633-9637.*
Rudikoff et al. Proc. Natl. Acad. Sci. USA, 1982, vol. 79, pp. 1979-1983.*
Ennis F et al. J. Infect. Dis. 2002, vol. 185, pp. 1657-1659.*
Demkowicz et al. J. Virol. 1993, vol. 67, No. 3, pp. 1538-1544.*

Lazar, E., et al., "Transforming Growth Factor α: Mutation of Aspartic Acid 47 and Leucine 48 Results in Different Biological Activities," *Mol. Cell. Biol*., 8(3): 1247-1252 (1988).

Skelton, N.J., et al., "Proton NMR Assignments and Solution Conformation of RANTES, a Chemokine of the C-C Type," *Biochemistry*, 34: 5329-5342 (1995).
Smilek, D.E., et al., "A Single Amino Acid Change in a Myelin Basic Protein Peptide Confers the CapaCity to Prevent Rather Than Induce Experimental Autoimmune Encephalomyelitis," *Proc. Natl. Acad. Sci. USA*, 88: 9633-9637 (1991).
Drexler, I., et al., "Identification of Vaccinia Virus Epitope-Specific HLA-A*0201-Restricted T Cells and Comparative Analysis of Smallpox Vaccines," *Proc. Natl. Acad. Sci. USA* 100(1):217-222 (Jan. 2003).

Terajima, M., et al., "Quantitation of CD8+T Cell Responses to Newly Identified HLA-A*0201-Restricted T Cell Epitopes Conserved Among Vaccinia and Variola (Smallpox) Viruses," *J. Exp. Med*. 197(7):927-932 (Apr. 2003).

Ramirez, J.C., et al., "Biology of Attenuated Modified Vaccinia Virus Ankara Recombinant Vector in Mice: Virus Fate and Activation of B- and T-Cell Immune Responses in Comparison With the Western Reserve Strain and Advantages as a Vaccine," *J. Virol*. 74(2):923-933 (Jan. 2000).

Gen Bank Acc. No. M35027 "Vaccinia Virus, Complete Genome," (1990, updated 2000).
Wagner, C., et al., "Identification of an HLA-A*02 Restricted Immunogenic Peptide Derived from the Cancer Testis Antigen HOM-MEL-40/SSX2," *Cancer Immunity* 3:18 (Dec. 2003).
Oseroff, C., et al., "HLA Class I-restricted Responses to Vaccinia Recognize a Broad Array of Proteins Mainly Involved in Virulence and Viral Gene Regulation," *Proc. Natl. Acad. Sci. USA* 102(39):13980-13985 (2005).
Carroll, M.W., et al., "Highly Attenuated Modified Vaccinia Virus Ankara (MVA) as an Effective Recombinant Vector: a Murine Tumor Model," *Vaccine* 15(4):387-394 (1997).

(Continued)

*Primary Examiner* — Bao Li
(74) *Attorney, Agent, or Firm* — Hamilton, Brook, Smith & Reynolds, P.C.

(57) ABSTRACT

The present invention relates to the identification of gene sequences and proteins involved in vaccinia virus dominant T cell epitopes. Three vaccinia virus $CD8^+$ T cell epitopes restricted by the most common human M.C. class I allele, HLA-A0201, were identified. Each of these epitopes is highly conserved in vaccinia and variola viruses. In addition, the induction of the T cell responses following primary vaccination with two of these epitopes is demonstrated by the kinetics of epitope specific $CD8^+$ T cells in 3 HLA-A0201 individuals. Two vaccinia virus $CD8^+$ T cell epitopes restricted by another common human M.C. class I allele, HLA-B7, also were identified. Both epitopes are highly conserved in vaccinia and variola viruses. This information will be useful for the design and analysis of the immunogenicity of experimental vaccinia vaccines, and for basic studies of human T cell memory.

23 Claims, 4 Drawing Sheets

OTHER PUBLICATIONS

Figure 1:
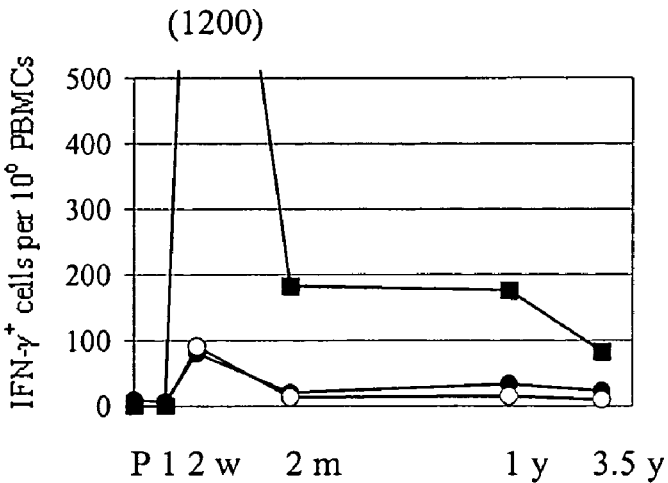
Figure 1:
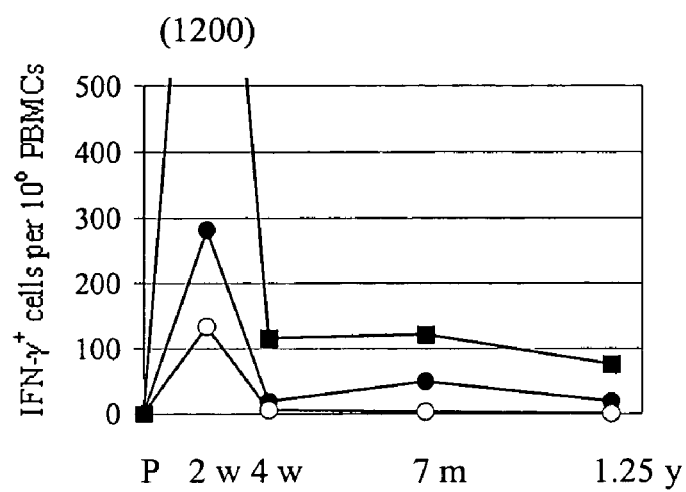
Figure 1:
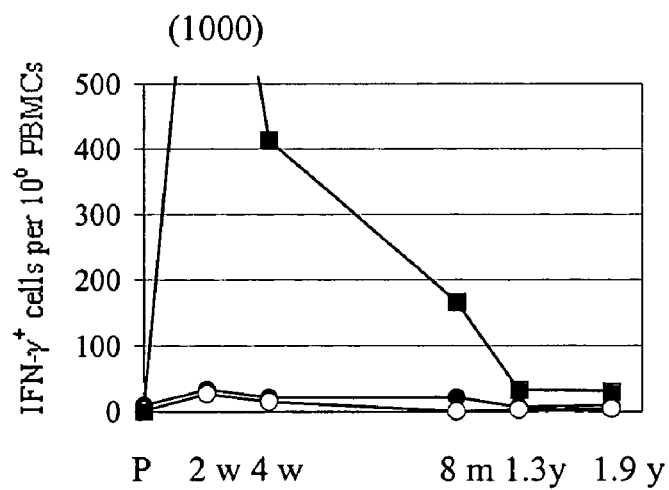

Carroll, M.W., and Moss, B., "Poxviruses as Expression Vectors," *Curr. Opin. Biotechnol.* 8(5):573-577 (1997).

DeLisi, C., et al., "T-cell Antigenic Sites Tend to be Amphipathic Structures," *Proc. Natl. Acad. Sci. USA* 82:7048-7052 (1985).

Bixler, Jr., G.S., and Atassi, M.Z., "T Cell Recognition of Myoglobin. Localization of the Sites Stimulating T Cell Proliferative Responses by Synthetic Overlapping Peptides Encompassing the Entire Molecule," *J. Immunogenet.* 11(5-6):339-353 (1984).

Geysen, H.M., et al., "The Delineation of Peptides Able to Mimic Assembled Epitopes," in *Synthetic as Antigens—Ciba Foundation Symposium* 119 (Porter, R., and Whelan, J., Eds.), pp. 130-149, John Wiley & Sons, Chichester (1986).

Mathew, A., et al., "Identification of Murine Poxvirus-specific $CD8^+$. CTL Epitopes with Distinct Functional Profiles," *J. Immunol.* 174:2212-2219 (2005).

Tscharke, D.C., et al., "Identification of Poxvirus $CD8^+$T Cell Determinants to Enable Rational Design and Characterization of Smallpox Vaccines," *J. Exp. Med.* 201(1):95-104 (2005).

Gen Bank Acc. No. Y16780, "Variola Minor Virus Complete Genome," (updated 2005), [online][retrieved on Nov. 14, 2005].

Gen Bank Acc. No. X69198, "Variola Virus DNA Complete Genome," (updated 2005), [online][retrieved on Nov. 14, 2005].

Gen Bank Acc. No. L22579, "Variola Major Virus (Strain Bangladesh—1995) Complete Genome," (1995), [online][retrieved on Nov. 14, 2005].

Gen Bank Acc. No. AF095689, "Vaccinia Virus (Strain Tian Tan) Complete Genome," (2000), [online][retrieved on Nov. 14, 2005].

Gen Bank Acc. No. M35027, "Vaccinia Virus Complete Genome," (1993), [online][retrieved on Nov. 14, 2005].

Gen Bank Acc. No. U94848, "Vaccinia Virus Strain Ankara, Complete Genomic Sequence," (2003), [online][retrieved on Nov. 14, 2005].

Gen Bank Acc. No. AF482758, "Cowpox Virus Strain Brighton Red, Complete Genome," (2003), [online][retrieved on Nov. 14, 2005].

Gen Bank Acc. No. AF380138, "Monkeypox Virus Strain Zaire-96-I-16, Complete Genome," (2001), [online][retrieved on Nov. 14, 2005].

Gen Bank Acc. No. X94355, "Cowpox Virus Strain GRI-90, Complete Genome," (2005), [online][retrieved on Nov. 14, 2005].

Bixler, G.S. and Atassi, M.Z., "Molecular Localization of the Full Profile of the Continuous Regions Recognized by Myoglobin Primed T-Cells Using Synthetic Overlapping Peptides Encompassing the Entire Molecule," *Immunological Communications* 12(6):593-603 (1983).

Feb. 27, 2009, Final Office Action, 11 pages, U.S. Appl. No. 11/731,784.

Dec. 10, 2008, Amendment, U.S. Appl. No. 11/731,784.

May 1, 2009, Amendment after Final Rejection, U.S. Appl. No. 11/731,784.

Jun. 10, 2009, Examiner Interview Summary Record (PTOL-413), U.S. Appl. No. 11/731,784.

Jun. 18, 2009, Advisory Action (PTOL-303), U.S. Appl. No. 11/731,784.

Jun. 24, 2009, Examiner Interview Summary Record (PTOL-413), U.S. Appl. No. 11/731,784.

Aug. 21, 2009, Supplemental Response, U.S. Appl. No. 11/731,784.

Dec. 12, 2009, Examiner Interview Summary Record (PTOL-413), U.S. Appl. No. 11/731,784.

Feb. 26, 2010, Amendment, U.S. Appl. No. 11/731,784.

Apr. 30, 2010, Examiner Interview Summary Record (PTOL-413), U.S. Appl. No. 11/731,784.

Apr. 30, 2010, Notice of Allowance, U.S. Appl. No. 11/731,784.

Aug. 11, 2005, Notification Concerning Transmittal of International Preliminary Report on Patentability and International Preliminary Report on Patentability, PCT/US2004/002141.

Nov. 11, 2009, Result of Consultation by telephone with the applicant / representative, EP 04 705 315.2.

Dec. 4, 2009, Letter accompanying subsequently filed items and matter concerning the application, EP 04 705 315.2.

Jan. 19, 2010, Communication pursuant to Article 94(3) EPC, EP 04 705 315.2.

\* cited by examiner

74A

165

Preimmune     2 weeks     1 year

CD8
└── Tetramer

Donor 1

Donor 2

Donor 3

SEQUENCE LISTING

```
<160> NUMBER OF SEQ ID NOS: 42

<210> SEQ ID NO 1
<211> LENGTH: 9
<212> TYPE: PRT
<213> ORGANISM: Unknown
<220> FEATURE:
<223> OTHER INFORMATION: 74A peptide of MVA

<400> SEQUENCE: 1

Cys Leu Thr Glu Tyr Ile Leu Trp Val
 1               5

<210> SEQ ID NO 2
<211> LENGTH: 9
<212> TYPE: PRT
<213> ORGANISM: Unknown
<220> FEATURE:
<223> OTHER INFORMATION: 165 peptide of MVA

<400> SEQUENCE: 2

Lys Val Asp Asp Thr Phe Tyr Tyr Val
 1               5

<210> SEQ ID NO 3
<211> LENGTH: 9
<212> TYPE: PRT
<213> ORGANISM: Unknown
<220> FEATURE:
<223> OTHER INFORMATION: 165 peptide of Monkeypox (Zaire-96-I-16)

<400> SEQUENCE: 3

Lys Val Asp Tyr Thr Leu Tyr Tyr Val
 1               5

<210> SEQ ID NO 4
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 4

Ile Leu Thr Glu Tyr Ile Leu Trp Val
 1               5

<210> SEQ ID NO 5
<211> LENGTH: 9
```

```
<212> TYPE: PRT
<213> ORGANISM: Unknown
<220> FEATURE:
<223> OTHER INFORMATION: Possible mutant of 74A peptide

<400> SEQUENCE: 5

Leu Leu Thr Glu Tyr Ile Leu Trp Val
 1               5

<210> SEQ ID NO 6
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 6

Phe Leu Thr Glu Tyr Ile Leu Trp Val
 1               5

<210> SEQ ID NO 7
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 7

Cys Leu Ala Glu Tyr Ile Leu Trp Val
 1               5

<210> SEQ ID NO 8
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 8

Cys Leu Tyr Glu Tyr Ile Leu Trp Val
 1               5

<210> SEQ ID NO 9
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 9

Cys Leu Phe Glu Tyr Ile Leu Trp Val
 1               5

<210> SEQ ID NO 10
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 10

Cys Leu Thr Glu Ile Ile Leu Trp Val
 1               5

<210> SEQ ID NO 11
<211> LENGTH: 9
<212> TYPE: PRT
<213> ORGANISM: Unknown
```

```
<220> FEATURE:
<223> OTHER INFORMATION: Possible mutant of 74A peptide

<400> SEQUENCE: 11

Cys Leu Thr Glu Lys Ile Leu Trp Val
 1               5

<210> SEQ ID NO 12
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 12

Cys Leu Thr Glu Asn Ile Leu Trp Val
 1               5

<210> SEQ ID NO 13
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 13

Cys Leu Thr Glu Tyr Ile Ala Trp Val
 1               5

<210> SEQ ID NO 14
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 14

Cys Leu Thr Glu Tyr Ile Tyr Trp Val
 1               5

<210> SEQ ID NO 15
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 15

Cys Leu Thr Glu Tyr Ile His Trp Val
 1               5

<210> SEQ ID NO 16
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 16

Ile Leu Ala Glu Tyr Ile Leu Trp Val
 1               5

<210> SEQ ID NO 17
<211> LENGTH: 9
<212> TYPE: PRT
<213> ORGANISM: Unknown
<220> FEATURE:
<223> OTHER INFORMATION: Possible mutant of 74A peptide
```

```
<400> SEQUENCE: 17

Ile Leu Ala Glu Ile Ile Leu Trp Val
1               5

<210> SEQ ID NO 18
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 18

Ile Leu Ala Glu Ile Ile Ala Trp Val
1               5

<210> SEQ ID NO 19
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 19

Ile Val Asp Asp Thr Phe Tyr Tyr Val
1               5

<210> SEQ ID NO 20
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 20

Leu Val Asp Asp Thr Phe Tyr Tyr Val
1               5

<210> SEQ ID NO 21
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 21

Phe Val Asp Asp Thr Phe Tyr Tyr Val
1               5

<210> SEQ ID NO 22
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 22

Lys Val Ala Asp Thr Phe Tyr Tyr Val
1               5

<210> SEQ ID NO 23
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 23
```

Lys Val Tyr Asp Thr Phe Tyr Tyr Val
1               5

<210> SEQ ID NO 24
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 24

Lys Val Phe Asp Thr Phe Tyr Tyr Val
1               5

<210> SEQ ID NO 25
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 25

Lys Val Asp Asp Ile Phe Tyr Tyr Val
1               5

<210> SEQ ID NO 26
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 26

Lys Val Asp Asp Lys Phe Tyr Tyr Val
1               5

<210> SEQ ID NO 27
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 27

Lys Val Asp Asp Tyr Phe Tyr Tyr Val
1               5

<210> SEQ ID NO 28
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 28

Lys Val Asp Asp Thr Phe Ala Tyr Val
1               5

<210> SEQ ID NO 29
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 29

Lys Val Asp Asp Thr Phe His Tyr Val

<210> SEQ ID NO 30
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 30

Ile Val Ala Asp Thr Phe Tyr Tyr Val
1               5

<210> SEQ ID NO 31
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 31

Ile Val Ala Asp Ile Phe Tyr Tyr Val
1               5

<210> SEQ ID NO 32
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 32

Ile Val Ala Asp Ile Phe Ala Tyr Val
1               5

<210> SEQ ID NO 33
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 33

Leu Val Tyr Asp Lys Phe His Tyr Val
1               5

<210> SEQ ID NO 34
<211> LENGTH: 9
<212> TYPE: PRT
<213> ORGANISM: Unknown
<220> FEATURE:
<223> OTHER INFORMATION: Viral T cell epitope

<400> SEQUENCE: 34

Leu Leu Tyr Ala His Ile Asn Ala Leu
1               5

<210> SEQ ID NO 35
<211> LENGTH: 9
<212> TYPE: PRT
<213> ORGANISM: Unknown
<220> FEATURE:
<223> OTHER INFORMATION: Viral T cell epitope

<400> SEQUENCE: 35

Thr Val Ala Asp Val Arg His Cys Leu
1               5

```
<210> SEQ ID NO 36
<211> LENGTH: 9
<212> TYPE: PRT
<213> ORGANISM: Unknown
<220> FEATURE:
<223> OTHER INFORMATION: Viral T cell epitope

<400> SEQUENCE: 36

Met Pro Ala Tyr Ile Arg Asn Thr Leu
1               5

<210> SEQ ID NO 37
<211> LENGTH: 9
<212> TYPE: PRT
<213> ORGANISM: Unknown
<220> FEATURE:
<223> OTHER INFORMATION: Viral T cell epitope

<400> SEQUENCE: 37

Leu Leu Tyr Thr His Ile Asn Ala Leu
1               5

<210> SEQ ID NO 38
<211> LENGTH: 9
<212> TYPE: PRT
<213> ORGANISM: Unknown
<220> FEATURE:
<223> OTHER INFORMATION: Viral T cell epitope

<400> SEQUENCE: 38

Leu Leu His Ala His Ile Asn Ala Leu
1               5

<210> SEQ ID NO 39
<211> LENGTH: 9
<212> TYPE: PRT
<213> ORGANISM: Unknown
<220> FEATURE:
<223> OTHER INFORMATION: Viral T cell epitope

<400> SEQUENCE: 39

Leu Leu Tyr Ala Asn Ile Asn Ala Leu
1               5

<210> SEQ ID NO 40
<211> LENGTH: 9
<212> TYPE: PRT
<213> ORGANISM: Unknown
<220> FEATURE:
<223> OTHER INFORMATION: Viral T cell epitope

<400> SEQUENCE: 40

Thr Val Asp Asp Ile Lys His Cys Leu
1               5

<210> SEQ ID NO 41
<211> LENGTH: 9
<212> TYPE: PRT
<213> ORGANISM: Unknown
<220> FEATURE:
<223> OTHER INFORMATION: Viral T cell epitope

<400> SEQUENCE: 41

Thr Val Thr Asp Val Arg His Cys Leu
1               5

<210> SEQ ID NO 42
```

```
<211> LENGTH: 9
<212> TYPE: PRT
<213> ORGANISM: Unknown
<220> FEATURE:
<223> OTHER INFORMATION: Viral T cell epitope

<400> SEQUENCE: 42

Met Pro Thr Tyr Ile Arg Asn Thr Leu
1               5
```

US 8,067,535 B2

IDENTIFICATION OF GENE SEQUENCES AND PROTEINS INVOLVED IN VACCINIA VIRUS DOMINANT T CELL EPITOPES

RELATED APPLICATION

This application is a continuation-in-part of U.S. application Ser. No. 10/764,985, filed Jan. 26, 2004, now U.S. Pat. No. 7,217,526, which claims the benefit of U.S. Provisional Application No. 60/442,846, filed Jan. 24, 2003. The entire teachings of the above applications are incorporated herein by reference.

GOVERNMENT SUPPORT

The invention was supported, in whole or in part, by grants PO1 AI-49320, U19 AI-057319 and subcontracts, AI-46725 and AI-46725, from the National Institutes of Health/National Institute of Allergy and Infectious Diseases (NIH/NIAID). The Government has certain rights in the invention.

BACKGROUND OF THE INVENTION

Immunization with vaccinia virus resulted in long-lasting protection against smallpox and was the successful approach used to eliminate natural smallpox infections worldwide. This accomplishment was achieved without a detailed understanding of human T cell responses to poxviruses. Due to the concern about the potential use of smallpox virus as a bioweapon, smallpox vaccination is currently being reintroduced. However, severe and life threatening complications from vaccination were associated with congenital or acquired T cell deficiencies, but not with congenital agammaglobulinemia. Considering the high incidence of side effects from current smallpox vaccine, the development of a safer, but equally effective vaccine is very important. Thus, it is important to have a detailed understanding of human T cell responses to poxviruses.

Vaccinia-specific CD4+ and CD8+ T cells have been detected in humans and the number of vaccinia virus-specific T cell responses to smallpox vaccine have been measured. Additionally, an intracellular cytokine staining assay was applied to quantitate and characterize vaccinia-specific T cells in mice. However, no T cell epitopes have been identified in humans or mice systems. One major obstacle is the size of the virus. Vaccinia is a large virus with an approximately 200-kbp DNA genome that has approximately 200 open reading frames.

In order to analyze T cell responses to licensed and experimental smallpox vaccines at the single cell level, it is essential to identify CD8+ T cell epitopes. In addition to emphasizing the importance of T cells in the immunity to smallpox, there is a critical need to develop new vaccines safe for use in T cell deficient populations. This information will be useful for the design and analyses of the immunogenicity of experimental vaccinia vaccines, and for basic studies of human T cell memory.

SUMMARY OF THE INVENTION

The present invention relates to the identification of gene sequences and proteins involved in vaccinia virus dominant T cell epitopes. Accordingly, the present invention provides methods for immunizing an individual in need thereof against infection by a vaccinia virus, a variola virus and/or a related poxvirus. In one embodiment, the invention provides a method for immunizing an individual against infection by vaccinia and/or variola virus, the method comprising inducing an immune response against a polypeptide comprising peptide 74A. In this embodiment, the polypeptide can be selected from the group consisting of MVA189R, Copenhagen B22R, Copenhagen C16L, Bangladesh-1975 D2L, India-1967 D1L, Garcia-1966 B1L, Brighton Red V212 or Zaire-96-I-16 N1R or other homologues of vaccinia and variola virus. In another embodiment, the method can further comprise one or more additional polypeptides that comprise a peptide selected from the group consisting of: peptide 165, peptide 029D, peptide B7080, peptide B7034 and immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide 165. In this embodiment, the polypeptide can be selected from the group consisting of MVA018L, Copenhagen C7L, Tian Tan TC7L, Bangladesh-1975 D11L, India-1967 D8L, Garcia-1966 B14L, Brighton Red V028 or Zaire-96-I-16 D10L or other homologues of vaccinia and variola virus. In an additional embodiment, the method can further comprise one or more additional polypeptides that comprise a peptide selected from the group consisting of: peptide 74A, peptide 029D, peptide B7080, peptide B7034 and immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

In yet another embodiment, the invention provides a method for immunizing an individual against infection by vaccinia and/or variola virus, the method comprising inducing an immune response against a polypeptide comprising peptide 029D. In this embodiment, the polypeptide can be selected from the group consisting of MVA160L, Copenhagen A47L, Bangladesh-1975 J1L, India-1967 J1L, Garcia-1966 K1L, GRI-90 A50L or Brighton Red CPXV185 or other homologues of vaccinia and variola virus. In another embodiment, the method can further comprise one or more additional polypeptides that comprise a peptide selected from the group consisting of: peptide 74A, peptide 165, peptide B7080, peptide B7034 and immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

In an additional embodiment, the present invention relates to a method for immunizing an individual against infection by vaccinia and/or variola virus, the method comprising inducing an immune response against a polypeptide comprising peptide B7080. In this embodiment, the polypeptide can be selected from the group consisting of MVA189R, Copenhagen B22R(C16L), Bangladesh-1975 D2L, India-1967 D1L, Garcia-1966 B1L, GRI-90 D5L (I1R), Brighton Red CPXV009 (CPXV222) or Zaire-96-I-16 N1R or other homologues of vaccinia and variola virus. In a further embodiment, the method can further comprise one or more additional polypeptides that comprise a peptide selected from the group consisting of: peptide 74A, peptide 165, peptide 029D, peptide B7034 and immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

In a further embodiment, the present invention relates to a method for immunizing an individual against infection by vaccinia and/or variola virus, the method comprising inducing an immune response against a polypeptide comprising peptide B7034. In this embodiment, the polypeptide can be selected from the group consisting of MVA090R, Copenhagen J6R, Bangladesh-1975 L6R, India-1967 L6R, Garcia-1966 M6R, GRI-90 O4R, Brighton Red CPXV109 or Zaire-96-I-16 L6R or other homologues of vaccinia and variola virus. In a further embodiment, the method can further comprise one or more additional polypeptides that comprise a peptide selected from the group consisting of: peptide 74A, peptide 165, peptide 029D, peptide B7080 and immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide 74A, immunogenic fragments and/or mutants thereof. From 1 to about 4 amino acids can be substituted to make up the immunogenic fragments or mutants of peptide 74A, without essentially detracting from the immunological properties of peptide 74A. In this embodiment, the polypeptide can be selected from the group consisting of MVA189R, Copenhagen B22R, Copenhagen C16L, Bangladesh-1975 D2L, India-1967 D1L, Garcia-1966 B1L, Brighton Red V212 or Zaire-96-I-16 N1R or other homologues of vaccinia and variola virus. In another embodiment, the method can further comprise one or more additional polypeptides comprising a peptide selected from the group consisting of 165, 029D, B7080, B7034 and immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide 165, immunogenic fragments and/or mutants thereof. From 1 to about 4 amino acids can be substituted to make up the immunogenic fragments or mutants of peptide 165, without essentially detracting from the immunological properties of peptide 165. For example, as shown in Table 1, amino acid changes can be made at positions 4 and/or 6 of the 165 epitope sequence depicted by SEQ ID NO: 2. In this embodiment, the polypeptide can be selected from the group consisting of MVA018L, Copenhagen C7L, Tian Tan TC7L, Bangladesh-1975 D11L, India-1967 D8L, Garcia-1966 B14L, Brighton Red V028 or Zaire-96-I-16 D10L or other homologues of vaccinia and variola virus. In another embodiment, the method can further comprise one or more additional polypeptides comprising a peptide selected from the group consisting of 74A, 029D, B7080, B7034 and immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide 029D, immunogenic fragments and/or mutants thereof. From 1 to about 4 amino acids can be substituted to make up the immunogenic fragments or mutants of peptide 029D, without essentially detracting from the immunological properties of peptide 029D. For example, as shown in Table 2, conservative amino acid changes can be made at positions 3, 4 or 5 of the 029D epitope sequence depicted by SEQ ID NO: 34. In this embodiment, the polypeptide can be selected from the group consisting of MVA160L, Copenhagen A47L, Bangladesh-1975 J1L, India-1967 J1L, Garcia-1966 K1L, GRI-90 A50L or Brighton Red CPXV185 or other homologues of vaccinia and variola virus. In yet another embodiment, the method can further comprise one or more additional polypeptides comprising a peptide selected from the group consisting of 74A, 165, B7080, B7034 and immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide B7080, immunogenic fragments and/or mutants thereof. From 1 to about 4 amino acids can be substituted to make up the immunogenic fragments or mutants of peptide B7080, without essentially detracting from the immunological properties of peptide B7080. For example, as shown in Table 2, amino acid changes can be made at positions 3, 5 and/or 6 of the B7080 epitope sequence depicted by SEQ ID NO: 35. In this embodiment, the polypeptide can be selected from the group consisting of MVA189R, Copenhagen B22R (C16L), Bangladesh-1975 D2L, India-1967 D1L, Garcia-1966 B1L, GRI-90 D5L (I1R), Brighton Red CPXV009 (CPXV222) or Zaire-96-I-16 N1R or other homologues of vaccinia and variola virus. In another embodiment, the method can further comprise one or more additional polypeptides comprising a peptide selected from the group consisting of: 74A, 165, 029D, B7034 and immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

In an additional embodiment, the present invention relates to a method for immunizing an individual against infection by vaccinia and/or variola virus, the method comprising inducing an immune response against a polypeptide comprising peptide B7034, immunogenic fragments and/or mutants thereof. From 1 to about 4 amino acids can be substituted to make up the immunogenic fragments or mutants of peptide B7034, without essentially detracting from the immunological properties of peptide B7034. For example, as shown in Table 2, amino acid changes can be made at position 3 of the B7034 epitope sequence depicted by SEQ ID NO: 36. In this embodiment, the polypeptide can be selected from the group consisting of MVA090R, Copenhagen J6R, Bangladesh-1975 L6R, India-1967 L6R, Garcia-1966 M6R, GRI-90 O4R, Brighton Red CPXV109 or Zaire-96-I-16 L6R or other homologues of vaccinia and variola virus. In another embodiment, the method can further comprise one or more additional polypeptides comprising a peptide selected from the group consisting of: 74A, 165, 029D, B7080 and immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the invention encompasses a method for inducing an immune response against vaccinia and/or variola virus in an individual, comprising administering to the individual a composition comprising one or more isolated polypeptides that comprise a peptide selected from the group consisting of peptide 74A, peptide 165, peptide 029D, peptide B7080, peptide B7034, variants thereof, immunogenic fragments thereof and mutants thereof, and optionally an adjuvant, whereby an immune response is induced against vaccinia and/or variola virus in the individual. In a particular embodiment, the composition consists essentially of one or more isolated polypeptides that comprise a peptide selected from the group consisting of peptide 74A, peptide 165, peptide 029D, peptide B7080, peptide B7034, variants thereof, immunogenic fragments thereof and mutants thereof, and optionally an adjuvant. In a certain embodiment, the adjuvant is alum.

In a related embodiment, the invention provides a method for inducing an immune response against vaccinia and/or variola virus in an individual, comprising administering to the individual a composition comprising one or more isolated nucleic acid molecules, wherein the one or more isolated nucleic acid molecules encodes a polypeptide that comprises a peptide selected from the group consisting of peptide 74A, peptide 165, peptide 029D, peptide B7080, peptide B7034, variants thereof, immunogenic fragments thereof and mutants thereof, whereby an immune response is induced against vaccinia and/or variola virus in the individual. In a particular embodiment, the nucleic acid is in a vector. In a certain embodiment, the composition consists essentially of one or more isolated nucleic acid molecules, wherein the one or more isolated nucleic acid molecules encodes a polypeptide that comprises a peptide selected from the group consisting of peptide 74A, peptide 165, peptide 029D, peptide B7080, peptide B7034, variants thereof, immunogenic fragments thereof and mutants thereof.

The present invention also relates to a method of identifying the presence of all, or an immunogenic portion of, a vaccinia, a variola and/or other related poxvirus in a sample comprising determining whether T cells present in the sample (e.g., blood, lymph and tissue) become activated in the presence of a polypeptide selected from the group consisting of: peptide 74A (SEQ ID NO: 1), peptide 165 (SEQ ID NO: 2), peptide 029D (SEQ ID NO: 34), peptide B7080 (SEQ ID NO: 35), peptide B7034 (SEQ ID NO:36) and combinations thereof, wherein if the T cells become activated, then all, or an immunogenic portion of, a vaccinia, a variola and/or other related poxvirus is present in the sample. In a particular embodiment, the invention provides a method of identifying the presence of all, or an immunogenic portion of, a vaccinia, a variola and/or other related poxvirus in a sample, comprising contacting the sample with T cells that become activated in the presence of one or more peptides selected from the group consisting of: peptide 74A, peptide 165, peptide 029D, peptide B7080, peptide B7034, a mutant thereof and an immunogenic fragment thereof, thereby producing a combination. The combination is maintained under conditions in which the T cells can become activated in the presence of the one or more peptides, wherein if the T cells become activated, then all or an immunogenic portion of a vaccinia, a variola, and/or a related poxvirus is present in the sample. In yet another embodiment, the invention is directed to a method of identifying whether T cells present in a sample have been contacted (e.g., previously contacted) with all or an immunogenic portion of a vaccinia, a variola and/or a related poxvirus, comprising contacting the T cells with one or more peptides selected from the group consisting of: peptide 74A, peptide 165, peptide 029D, peptide B7080, peptide B7034, a mutant thereof and an immunogenic fragment thereof, thereby producing a combination. The combination is maintained under conditions in which the T cells can become activated in the presence of the one or more peptides, wherein if the T cells become activated, then the T cells have been contacted with all or an immunogenic portion of a vaccinia, a variola, and/or a related poxvirus. Whether the T cells present in the sample become activated can be determined using, for example, a cytokine assay (e.g., ELISPOT), a flow cytometry assay (e.g., tetramer staining assay) and/or a limiting dilution assay.

T cells can be present in the original sample or can be added to the sample. For example, the sample can be blood which contains T cells. In this embodiment, whether the T cells become activated in the presence of the polypeptide is determined, wherein if the T cells become activated, then all, or an immunogenic portion of, a vaccinia, a variola and/or other related poxvirus is present in the sample and/or the T cells in the sample have been contacted with all, or an immunogenic portion of, a vaccinia, a variola and/or other related poxvirus. In another embodiment, the sample does not initially contain T cells. In this embodiment, the sample is contacted with T cells that become activated in the presence of all, or an immunogenic portion of, a vaccinia, a variola and/or other related poxvirus. Then whether the T cells become activated in the presence of the polypeptide is determined, wherein if the T cells become activated, then all, or an immunogenic portion of, a vaccinia, a variola and/or other related poxvirus is present in the sample.

The present invention also relates to a method of determining whether an individual has been infected with all, or an immunogenic portion of, a vaccinia, a variola and/or other related poxvirus comprising determining whether the individual's T cells become activated in the presence of polypeptide selected from the group consisting of: peptide 74A (SEQ ID NO: 1), peptide 165 (SEQ ID NO: 2), peptide 029D (SEQ ID NO: 34), peptide B7080 (SEQ ID NO: 35), peptide B7034 (SEQ ID NO:36) and combinations thereof, and wherein if the individual's T cells become activated in the presence of the peptide, then the individual has been infected with vaccinia, variola or other related poxvirus.

A method of monitoring the effectiveness of a vaccinia, variola or other related poxvirus vaccine in an individual who has been administered the vaccinia vaccine is also encompassed by the present invention. The method comprises determining whether the individual's T cells become activated in the presence of a polypeptide selected from the group consisting of: peptide 74A (SEQ ID NO: 1), peptide 165 (SEQ ID NO: 2), peptide 029D (SEQ ID NO: 34), peptide B7080 (SEQ ID NO: 35), peptide B7034 (SEQ ID NO:36) and combinations thereof, wherein if the individual's T cells become activated, then the vaccine is effective in the individual. In one embodiment, the vaccine is a vaccinia or variola virus vaccine. In a further embodiment, the vaccinia or variola virus vaccine is a cancer vaccine.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is a schematic depicting the kinetics of the frequency of IFN-γ-producing cells specific to these peptides and to whole vaccinia virus quantitated by IFN-γ ELISPOT assay using the peripheral blood mononuclear cells (PBMCs) of the vaccinia-immune donors. Closed circle: peptide 74A-specific cells. Open circle: peptide 165-specific cells. Closed square: vaccinia virus-specific cells. P: pre-immunization.

FIG. 2 depicts FACS staining to confirm specificity of MVA74A and MVA165 tetramers. HLA-A0201-negative donor PBMC was mixed with $CD8^+$ T cell clones specific for either the MVA74A or the MVA165 vaccinia virus epitope at a ratio of 10:1. Four color FACS analysis was done to determine the specificity. Cells are gated on CD3$^+$ CD4$^-$ cells with tetramer on the X-axis and CD8 on the y-axis.

Figure 3:
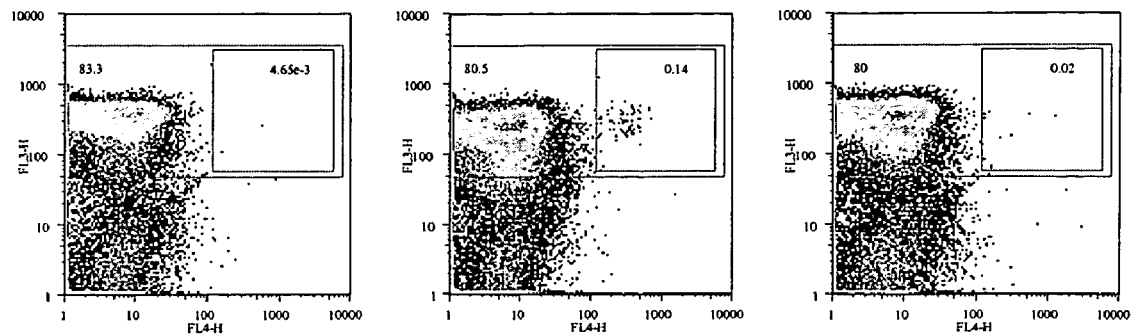
Figure 3:
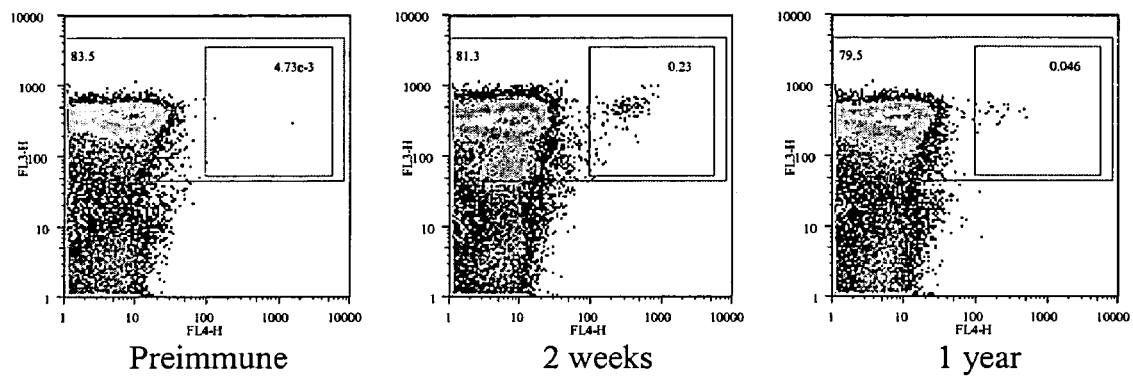

FIG. 3 is a schematic depicting the quantitation of vaccinia virus epitope-specific CD8$^+$ T cells by HLA-A0201/peptide 74A tetramer staining (top) and HLA-A0201/peptide 165 tetramer staining (bottom) of PBMCs of donor 1. Cells were gated on CD3$^+$ and CD4$^-$ cells with tetramer staining on the x-axis and CD8 on the y-axis. The larger squares show CD8$^+$ cells and the smaller squares show CD8$^+$ and tetramer$^+$ cells.

Figure 4:
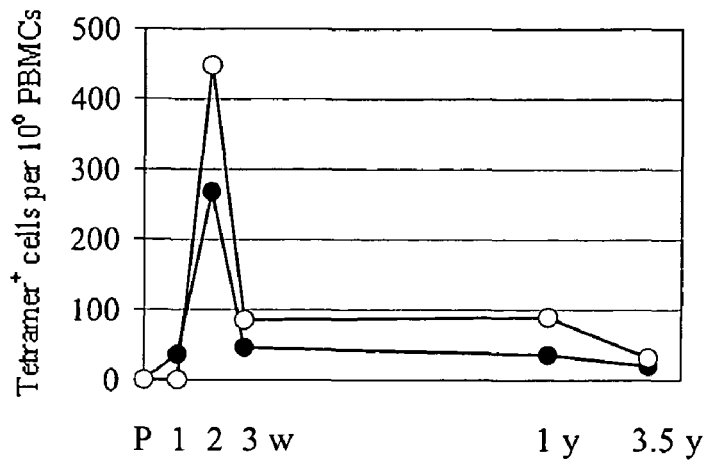
Figure 4:
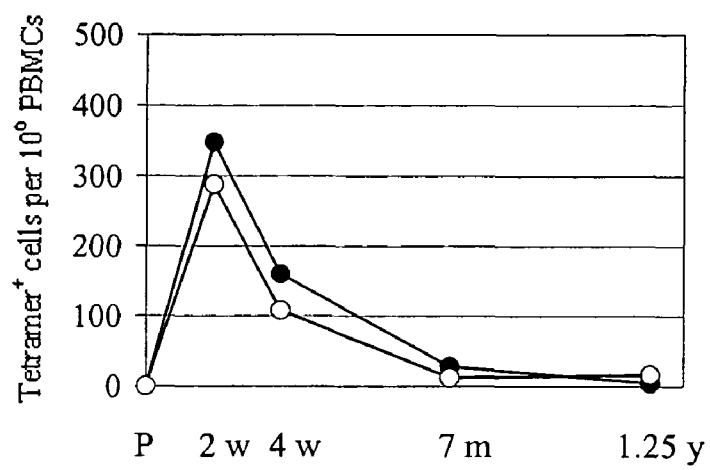
Figure 4:
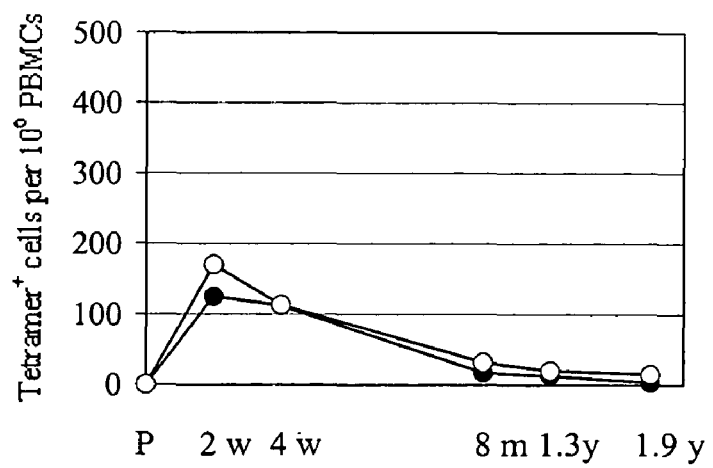

FIG. 4 is a schematic depicting the kinetics of the frequency of CD8$^+$ T cells specific for each epitope quantitated by tetramer staining in PBMCs of three donors after primary immunization. Closed circle: 74A-specific. Open circle: 165-specific. P: pre-immunization. Frequency is calculated per million PBMC for comparison with the data from epitope-specific IFN-γ ELISPOT assays.

DETAILED DESCRIPTION OF THE INVENTION

Successful vaccines deliver to a host one or more antigens derived from a pathogen, thereby stimulating an immune response which protects against subsequent challenge with the pathogen. Such vaccines can take a variety of forms, including attenuated or killed pathogens, for example, viruses or bacteria; one or more proteins or peptides derived from a pathogen or synthetic or recombinant versions of such proteins or peptides; or one or more nucleic acid molecules encoding one or more proteins or peptides from the pathogen, such as a naked DNA vaccine or a nucleic acid molecule administered in a suitable vector, such as a recombinant virus or bacterium or an immunostimulating complex. Vaccines against cell proliferative diseases, such as cancers, typically utilize proteins or fragments thereof, or nucleic acid molecules encoding proteins or fragments thereof, which are unique to diseased cells or generally more abundant in diseased cells compared to healthy cells.

Cell-mediated immunity is dependent upon lymphocytes known as B cells and T cells. B cells produce antibodies targeted against extracellular antigens. T cells recognize antigen fragments (peptides) which are displayed at the surface of a host cell. Such antigen fragments result from uptake of the antigen by a host cell, or synthesis of the antigen within the host cell, followed by cleavage of the antigen within the cell.

Foreign proteins which are synthesized within the host cell or are taken up by the host cell via specific receptors are fragmented within the cytosol of the cell. One or more of the resulting peptides can become associated with class I major histocompatibility molecules (MHC I), and the resulting complexes are then presented at the surface of the cell. These MHC I/peptide complexes are recognized by specific T cell receptors in certain CD8$^+$ T cells, and the peptides so presented are referred to as CD8 epitopes.

A foreign protein can be taken up by a host cell nonspecifically via endocytosis and then fragmented into peptides in a cellular lysosomal or endosomal compartment. One or more of these peptides can then become associated with a class II major histocompatibility molecule (MHC II) to form a complex which is then presented at the surface of the host cell. These MHC II/peptide complexes are recognized by CD4$^+$ T cells expressing a specific receptor which recognizes the MHC II/peptide complex. These peptides are referred to as CD4 epitopes.

Peripheral T cells in the blood and organs of the immune system (e.g. spleen and lymph nodes) exist in a quiescent or resting state. Upon interaction of T cells with an MHC/epitope complex, the T cells proliferate and differentiate into activated cells having a variety of functions. CD8$^+$ T cells typically become cytotoxic upon activation and destroy antigen-presenting cells via direct contact. Activated CD4$^+$ T cells provide a helper function to B cells, enabling B cells to differentiate into antibody-producing cells. Activated CD8$^+$ T cells and CD4$^+$ T cells release a variety of cytokines (lymphokines or interleukins), which can, for example, control differentiation of many classes of lymphocytic precursor cells.

Described herein are five vaccinia T cell epitopes. Three epitopes, 74A, 165 and 029D, are restricted by the HLA-A0201, the most common HLA allele (see Table 1 and Table 2), and the other epitopes, B7080 in the B22R protein and B7034 in the J6R protein, are restricted by the HLA-B7, another common HLA allele (see Table 2). These epitopes are conserved in vaccinia virus strains MVA and Copenhagen as well as in variola viruses. Furthermore, the data described herein demonstrate that there are at least two epitopes, one that is HLA-A*0201-restricted, and the other is HLA-B7-restricted, in the vaccinia protein B22R. Vaccinia protein A47L contains at least one human epitope restricted by HLA-A*0201, and two murine epitopes (Mathew et al. *The Journal of Immunology*, 2005, 174: 2212-2219, and Tscharke et al. *The Journal of Experimental Medicine*, 2005, 201: 95-104). Therefore, the B22R and A47L proteins may be immunodominant in vaccinia virus-induced CD8+ T cell responses.

The present invention relates to vaccinia virus-specific CD8$^+$ cytotoxic T lymphocyte (CTL) lines that were established by limiting dilution cloning from the peripheral blood mononuclear cells (PBMCs) of HLA-A0201-positive donors who received primary immunization with the licensed smallpox vaccine, Dryvax®. Among the highly polymorphic human MHC class I genes, HLA-A0201 was chosen to identify CD8$^+$ T cell epitopes because of the commonality of this allele among most ethnic groups. HLA-A0201 peptide binding motif searches was performed on all of the protein sequences of the modified vaccinia virus Ankara (MVA) strain (GenBank accession number U94848), which is being proposed for use as an attenuated smallpox vaccine and as a vector for vaccination against other infectious agents. The computer algorithm "HLA Peptide Binding Predictions" was used to calculate the binding affinity (score) of 9mer peptides to the HLA-A0201 molecule. It was hypothesized that early gene products may be more likely to have CD8$^+$ T cell epitopes, since in both humans and mice all of the known CD8$^+$ T cell epitopes to cytomegalovirus are encoded by immediate-early phase proteins. The early, early and late, and late genes in vaccinia were categorized by nucleotide sequence motifs, such as a late promoter or an early termination motif For initial screening all peptides with; (1) a binding score of more than a 1000 (70 peptides); or (2) a binding score of 100 to 999 and encoded by a gene expressed early or both early and late (125 peptides) were synthesized. A total of 195 peptides were screened using fifteen vaccinia virus-specific CTL lines. Two T cell epitopes were restricted by HLA-A0201 and cross-reactive to MVA.

One CTL line, VA55 3.13, recognized peptide 74A, CLTEYILWV (SEQ ID NO: 1), in a 21.7K protein encoded by a putative early and late gene, "189R", of the MVA strain with a calculated binding score of 3607. Another CTL line, VA49 3.12, recognized peptide 165, KVDDTFYYV (SEQ ID NO: 2), which is in a host range protein encoded by a putative early and late gene, "018L", with a calculated binding score of 365. FIG. 1 demonstrates the high level of specific recognition by these CTL lines of their respective epitope peptides (i.e., peptide 74A or peptide 165) in a dose response CTL experiment. These epitope sequences are highly-conserved in vaccinia and variola viruses (Table 1).

TABLE 1

Conservation of epitopes among poxviruses causing infection in humans.

| | GenBank accession # | Gene name | 74A peptide | Gene name | 165 peptide |
|---|---|---|---|---|---|
| Vaccinia | | | | | |
| MVA | U94848 | 189R | CLTEYILWV (SEQ ID NO: 1) | 018L | KVDDTFYYV (SEQ ID NO: 2) |
| Copenhagen | M35027 | B22R & C16L[b] | ********* | C7L | ********* |
| Tian Tan[a] | AF095689 | | | TC7L | ********* |
| Variola major | | | | | |
| Bangladesh-1975 | L22579 | D2L | ********* | D11L | ********* |
| India-1967 | X69198 | D1L | ********* | D8L | ********* |
| Variola minor | | | | | |
| Garcia-1966 | Y16780 | B1L | ********* | B14L | ********* |
| Cowpox | | | | | |
| Brighton Red | AF482758 | V212 | ********* | V028 | ********* |
| Monkeypox | | | | | |
| Zaire-96-I-16 | AF380138 | N1R | ********* | D10L | ***Y*L*** (SEQ ID NO: 3) |

Only strains of which the complete genome has been sequenced are listed.
* indicates an identical amino acid.
[a]Tian Tan strain does not have 189R orthologue according to the nucleotide sequence.
[b]Both genes are located within the inverted terminal repeats and the gene sequences are identical.

In addition, a third HLA-A2-restricted vaccinia T cell epitope was identified using this approach. In particular, VV-specific CD8+ CTL lines were established by limiting dilution cloning from peripheral blood mononuclear cells of an HLA-A2-positive donor who received primary immunization with the licensed smallpox vaccine, Dryvax®. CTL lines that were confirmed to be restricted by HLA-A2 were screened in cytotoxicity assays against a synthetic peptide library. This peptide library was synthesized based on the HLA-A0201 peptide binding motif searches performed on all of the protein sequences of the modified vaccinia virus Ankara strain (GenBank accession number U94848), and was used to identify the two HLA-A0201-restricted vaccinia T cell epitopes described herein above. One HLA-A2-restricted CTL line recognized a peptide, peptide 029D (LLYAHINAL; SEQ ID NO: 34), in a protein encoded by the "160L" gene of MVA. The sequence of this epitope is highly-conserved in vaccinia and variola viruses (Table 2).

TABLE 2

Conservation of HLA-2 and HLA-B7 epitopes among poxviruses causing infection in humans.

| | GenBank accession # | Gene name | 029D peptide | Gene name | B7080 peptide | Gene name | B7034 peptide |
|---|---|---|---|---|---|---|---|
| Vaccinia | | | | | | | |
| MVA | U94848 | MVA160L | LLYAHINAL (SEQ ID NO: 34) | MVA189R | TVADVRHCL (SEQ ID NO: 35) | MVA090R | MPAYIRNTL (SEQ ID NO: 36) |
| Copenhagen | M35027 | A47L | ********* | B22R(C16L) | ********* | J6R | ********* |
| Variola major | | | | | | | |
| Bangladesh-1975 | L22579 | J1L | *T*** (SEQ ID NO: 37) | D2L | ********* | L6R | ********* |
| India-1967 | X69198 | J1L | *T*** (SEQ ID NO: 37) | D1L | ********* | L6R | ********* |
| Variola minor | | | | | | | |
| Garcia-1966 | Y16780 | K1L | *T*** (SEQ ID NO: 37) | B1L | ********* | M6R | ********* |
| Cowpox | | | | | | | |
| GRI-90 | X94355 | A50L | H**** (SEQ ID NO: 38) | D5L (I1R) | ********* | O4R | ********* |
| Brighton Red | AF482758 | CPXV185 | **N (SEQ ID NO: 39) | CPXV009 (CPXV222) | D*IK* (SEQ ID NO: 40) | CPXV109 | ******* |

TABLE 2-continued

Conservation of HLA-2 and HLA-B7 epitopes among poxviruses causing infection in humans.

| | GenBank accession # | Gene name | 029D peptide | Gene name | B7080 peptide | Gene name | B7034 peptide |
|---|---|---|---|---|---|---|---|
| Monkeypox | | | | | | | |
| Zaire-96-I-16[a] | AF380138 | NA | | N1R | \*\*T\*\*\*\*\*\* (SEQ ID NO: 41) | L6R | \*\*T\*\*\*\*\*\* (SEQ ID NO: 42) |

Only strains for which the complete genome has been sequenced are listed.
[a]Zaire-96-I-16 strain does not have an A47L orthologue according to the nucleotide sequence.
\* indicates an identical amino acid.

The present invention also relates to vaccinia virus-specific CD8+ cytotoxic T lymphocyte (CTL) lines that were established by limiting dilution cloning from the peripheral blood mononuclear cells (PBMCs) of HLA-B7-positive donors who received primary immunization with the licensed smallpox vaccine, Dryvax®. Among the highly polymorphic human MHC class I genes, another common allele, HLA-B7, was chosen to identify CD8+ T cell epitopes. HLA-B7 peptide binding motif searches were performed on all of the protein sequences of the modified vaccinia virus Ankara (MVA) strain (GenBank accession number U94848) using the computer algorithm "HLA Peptide Binding Predictions" to calculate the binding affinity (score) of 9mer peptides to the HLA-B7 molecule. It was hypothesized that early gene products may be more likely to have CD8+ T cell epitopes. All peptides with: (1) a binding score of more than a 100 (35 peptides); or (2) a binding score of 10 to 99, which also were encoded by a gene expressed either early or both early and late (186 peptides), were synthesized.

A total of 221 peptides were screened using 13 vaccinia virus-specific CTL lines. Two HLA-B7-restricted CTL lines, which were established from the same donor, recognized a peptide, peptide B7080 (TVADVRHCL; SEQ ID NO: 35), in a protein encoded by the "189R" gene of MVA, and a peptide B7034 (MPAYIRNTL; SEQ ID NO: 36), in a protein encoded by the "090R" gene of MVA, respectively. These epitope sequences are highly-conserved in vaccinia and variola viruses (Table 2).

Epitope-specific T cell clones can be generated using methods which are generally known in the art (see, for example, Fathman, et al., in Paul, ed., *Fundamental Immunology*, second edition, Raven Press (1989), Chapter 30, the contents of which are hereby incorporated by reference in their entirety). The isolation of epitope-specific T cell clones is based on T cell biology. Generally, an animal, such as a mouse, is immunized with a preparation of antigens (a bacterial lysate, or a purified protein) or is infected with a virus, such as a wild type virus or a recombinant virus containing heterologous genes encoding one or more proteins from a pathogenic microorganism, such as a virus. The animal is then sacrificed and the peripheral blood mononuclear cells (PBMC: includes T cells, B cells, monocytes), spleen and lymph nodes are isolated. The isolated cells are then cultured in media containing a defined component of the original antigenic preparation, often a recombinant or purified protein, and the essential T cell growth factor interleukin-2 (IL-2). The only T cells which will proliferate are those which recognize MHC/epitope complex in which the epitope is derived from the antigenic preparation. These cells become activated and proliferate while the unactivated cells begin to die. The cultures are maintained for several weeks, with the media containing antigen and IL-2 being periodically replaced. Eventually, clusters of living and dividing cells (a T cell line) can be observed in some of the cultures. The proliferating cells are generally not clonal at this point and are of limited use for assaying epitope specific T cell responses. The T cell line is, preferably, cloned through a process referred to as limiting dilution. In this method, PBMC are isolated from, for example, the same strain as the original used to isolate the T cell line. These cells, called antigen presenting cells, will serve as a source of MHC proteins and will present the MHC: peptide complex to the T cell line. The T cell line is diluted to a concentration of about 1 to 5 T cells/mL in a suspension of APCs that contains the antigen of interest and IL-2. This suspension is then transferred into, for example, round or "v"-bottom 96 well microtitre plates, so that each well contains, on average, no more than 1 T cell. The cultures are maintained for several weeks and a clone can grow out of one or more cultures. The cells isolated by limiting dilution are the progeny of a single cell that expresses only one T cell receptor, and the clone is thus epitope-specific.

Figure 2:
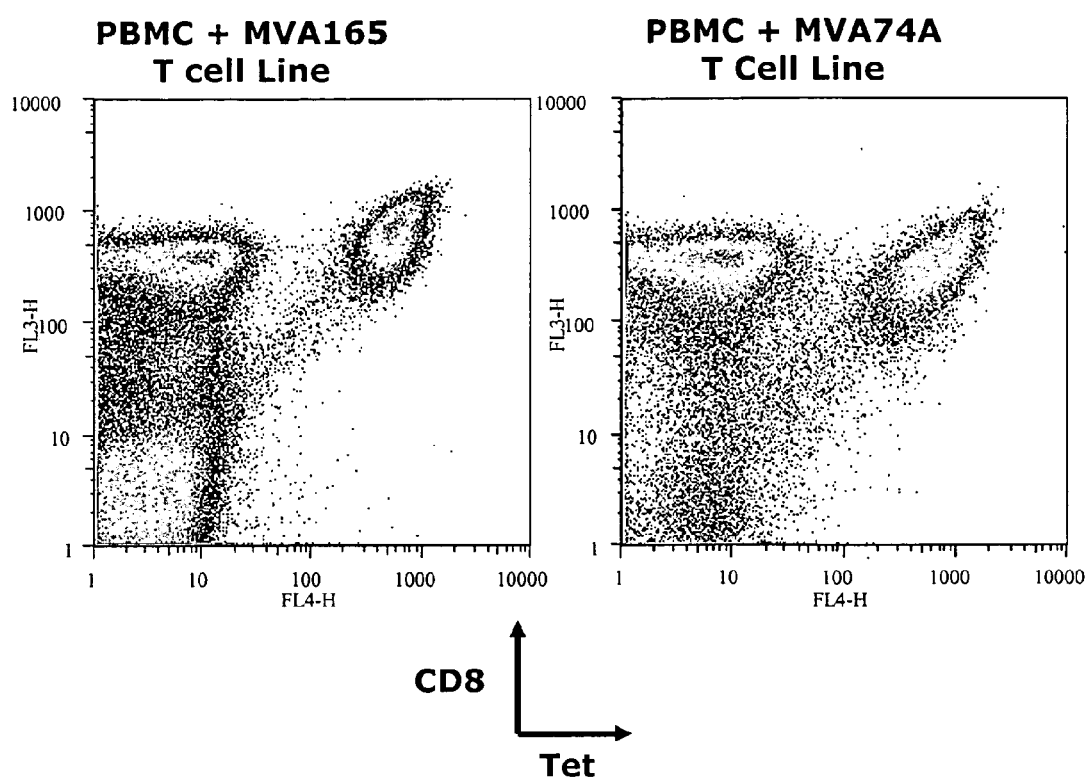

CD8+ T cells specific to epitopes 74A and 165 were measured at several time points following primary immunization by peptide/HLA-A0201 tetramer staining using the PBMCs of three HLA-A0201-positive donors. FIG. 2 shows representative FACS plots of donor 1 PBMC. In FIGS. 3 and 4, "preimmune" means prior to primary first immunization, and "two weeks" means two weeks after the second immunization for donor 3 who failed to "take" after primary immunization, and twenty days after primary immunization was immunized for the second time. In all three donors the frequency of vaccinia-specific CD8+ T cells peaked two weeks after primary immunization and then declined, but were still detectable one to three years following primary immunization (FIG. 3). Two weeks after vaccination the IFN-γ-producing cells specific to these two epitopes were 14% of total vaccinia virus-specific IFN-γ-producing cells in donor 1, 35% in donor 2, and 6% in donor 3 (FIG. 4).

Thus, three CD8+ T cell epitopes restricted by HLA-A0201, the most common MHC class I allele in humans, and two CD8+ T cell epitopes restricted by HLA-B7, another common allele, have been identified. These are the first T cell epitopes that have been reported for vaccinia virus. IFN-γ-producing cells specific to two of the HLA-A0201 epitopes represented 6 to 35% of total number of IFN-γ-producing cells specific to vaccinia virus. For these epitopes, the frequency of epitope-specific T cells was always higher by peptide/HLA tetramer staining than by IFN-γ-ELISPOT assay, although post-vaccination kinetics for each epitope-specific T cell was similar using both methods.

As for epitope selection, peptide 74A was the 15$^{th}$ highest binding peptide to HLA-A0201 of the 195 peptides selected for screening and peptide 165 was the 95$^{th}$ highest binder. One common characteristic of these two peptides is that they are both encoded by genes with a late promoter and an early termination motif, which means they may be expressed at both early and late phases of infection. The 189R gene of MVA strain encoding peptide 74A is a nonessential gene with unknown function. The 018L gene of MVA encoding peptide 165 is an orthologue of the host range protein, C7L, of the Copenhagen strain. Although selection of peptides was biased toward genes expressed in the early phase of infection, viral proteins produced in the early phase of infection may be processed and presented more efficiently by infected cells than those produced only in late phase, as a result of vaccinia virus down regulating host protein synthesis. These two epitopes are highly-conserved among variola viruses, suggesting the CTLs recognizing these epitopes will recognize variola virus-infected cells.

In another study, the frequency of T cell epitopes for each of the five identified peptides (74A, 165, 029D, B7080, B7034) was determined in donor PBMCs at 45 days after primary immunization using an IFN-γ-ELISPOT assay. The results of this study are shown in Table 3.

TABLE 3

Frequencies of epitope-specific T cells in donor PBMCs (IFN-γ producing cells/$10^6$ PBMCs) at 45 days after primary immunization.

| Donor | Donor B | Donor D | Donor E | Donor F | Donor G | Donor H | Donor I |
|---|---|---|---|---|---|---|---|
| HLA-A | 3, 11 | 2, 3 | 2, 3 | 2, 24 | 2, 3 | 2 | 2, 24 |
| HLA-B | 7, 44 | 7, 18 | 7, 27 | 7, 14 | 35, 44 | 35, 29 | 35, 57 |
| 74A (A2) | NT* | 10.7 | 9.3 | 6.7 | <u>150.7</u> | 0 | <u>36.0</u> |
| 165 (A2) | NT* | 13.3 | 22.7 | 10.7 | <u>50.7</u> | 1.3 | <u>118.7</u> |
| 029D (A2) | NT* | 9.3 | <u>77.3</u> | 9.3 | <u>26.7</u> | 0 | 0 |
| B7080 (B7) | 13.3 | 10.7 | <u>149.3</u> | 12.0 | <u>74.7</u> | 1.3 | 0 |
| B7034 (B7) | 5.3 | 16.0 | <u>196.0</u> | 0 | 18.6 | 0 | 2.7 |
| VV | <u>61.3</u> | <u>101.3</u> | <u>225.3</u> | 0 | NT† | <u>60.0</u> | <u>772.0</u> |

Numbers considered positive are underlined.
*Not tested because the donor was HLA-A2-negative.
†Not tested because of the limitation of the sample.
A2—A2 restricted
B7—B7 restricted
VV—Vaccinia virus In one embodiment, the invention provides a method for immunizing an individual against infection by vaccinia and/or variola virus, the method comprising inducing an immune response against a polypeptide comprising peptide 74A. In this embodiment, the polypeptide can be selected from the group consisting of MVA189R, Copenhagen B22R, Copenhagen C16L, Bangladesh-1975 D2L, India-1967 D1L, Garcia-1966 B1L, Brighton Red V212 or Zaire-96-I-16 N1R or other homologues of vaccinia and variola virus. In another embodiment, the method can further comprise one or more additional polypeptides comprising a peptide selected from the group consisting of 029D, 165, B7080 and B7034. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide 165. In this embodiment, the polypeptide can be selected from the group consisting of MVA018L, Copenhagen C7L, Tian Tan TC7L, Bangladesh-1975 D11L, India-1967 D8L, Garcia-1966 B14L, Brighton Red V028 or Zaire-96-I-16 D10L or other homologues of vaccinia and variola virus. In a further embodiment, the method can further comprise one or more additional polypeptides comprising a peptide selected from the group consisting of 74A, 029D, B7080 and B7034. In a further embodiment, the immune response is induced by administering a product selected from the group consisting of a polypeptide, a naked nucleic acid molecule encoding the peptide or a nucleic acid molecule, encoding the peptide, in a suitable vector.

In yet another embodiment, the invention provides a method for immunizing an individual against infection by vaccinia and/or variola virus, the method comprising inducing an immune response against a polypeptide comprising peptide 029D. In this embodiment, the polypeptide can be selected from the group consisting of MVA160L, Copenhagen A47L, Bangladesh-1975 J1L, India-1967 J1L, Garcia-1966 K1L, GRI-90 A50L or Brighton Red CPXV185 or other homologues of vaccinia and variola virus. In another embodiment, the method can further comprise one or more additional polypeptides comprising a peptide selected from the group consisting of 74A, 165, B7080 and B7034. In a further embodiment, the immune response is induced by administering a product selected from the group consisting of a polypeptide, a naked nucleic acid molecule encoding the peptide or a nucleic acid molecule, encoding the peptide, in a suitable vector.

In an additional embodiment, the present invention relates to a method for immunizing an individual against infection by vaccinia and/or variola virus, the method comprising inducing an immune response against a polypeptide comprising peptide B7080. In this embodiment, the polypeptide can be selected from the group consisting of MVA189R, Copenhagen B22R(C16L), Bangladesh-1975 D2L, India-1967 D1L, Garcia-1966 B1L, GRI-90 D5L (I1R), Brighton Red CPXV009 (CPXV222) or Zaire-96-I-16 N1R or other homologues of vaccinia and variola virus. In a further embodiment, the method can further comprise one or more additional polypeptides comprising a peptide selected from the group consisting of 74A, 165, 029D and B7034. In a further embodiment, the immune response is induced by administering a product selected from the group consisting of a polypeptide, a naked nucleic acid molecule encoding the peptide or a nucleic acid molecule, encoding the peptide, in a suitable vector.

In yet an additional embodiment, the present invention relates to a method for immunizing an individual against infection by vaccinia and/or variola virus, the method comprising inducing an immune response against a polypeptide comprising peptide B7034. In this embodiment, the polypeptide can be selected from the group consisting of MVA090R, Copenhagen J6R, Bangladesh-1975 L6R, India-1967 L6R, Garcia-1966 M6R, GRI-90 O4R, Brighton Red CPXV109 or Zaire-96-I-16 L6R or other homologues of vaccinia and variola virus. In a further embodiment, the method can further comprise one or more additional polypeptides comprising a peptide selected from the group consisting of 74A, 165, 029D and B7080. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide 74A, immunogenic fragments or mutants thereof. From 1 to about 4 amino acids can be substituted to make up the immunogenic fragments or mutants of peptide 74A, without essentially detracting from the immunological properties of peptide 74A. In this embodiment, the polypeptide can be selected from the group consisting of MVA189R, Copenhagen B22R, Copenhagen C16L, Bangladesh-1975 D2L, India-1967 D1L, Garcia-1966 B1L, Brighton Red V212 or Zaire-96-I-16 N1R or other homologues of vaccinia and variola virus. In another embodiment, the method can further comprise one or more additional polypeptides comprising a peptide selected from the group consisting of 029D, 165, B7080, B7034, and immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide 165, immunogenic fragments or mutants thereof. From 1 to about 4 amino acids can be substituted to make up the immunogenic fragments or mutants of peptide 165, without essentially detracting from the immunological properties of peptide 165. For example, as shown in Table 1, amino acid changes can be made at positions 4 and/or 6 of the 165 epitope sequence depicted by SEQ ID NO: 2. In this embodiment, the polypeptide can be selected from the group consisting of MVA018L, Copenhagen C7L, Tian Tan TC7L, Bangladesh-1975 D11L, India-1967 D8L, Garcia-1966 B14L, Brighton Red V028 or Zaire-96-I-16 D10L or other homologues of vaccinia and variola virus. In another embodiment, the method can further comprise one or more additional polypeptides comprising a peptide selected from the group consisting of 74A, 029D, B7080 and B7034, and immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide 029D, immunogenic fragments or mutants thereof. From 1 to about 4 amino acids can be substituted to make up the immunogenic fragments or mutants of peptide 029D, without essentially detracting from the immunological properties of peptide 029D. For example, as shown in Table 2, conservative amino acid changes can be made at positions 3, 4 or 5 of the 029D epitope sequence depicted by SEQ ID NO: 34. In this embodiment, the polypeptide can be selected from the group consisting of MVA160L, Copenhagen A47L, Bangladesh-1975 J1L, India-1967 J1L, Garcia-1966 K1L, GRI-90 A50L or Brighton Red CPXV185 or other homologues of vaccinia and variola virus. In another embodiment, the method can further comprise one or more additional polypeptides comprising a peptide selected from the group consisting of 74A, 165, B7080, B7034 and immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide B7080, immunogenic fragments or mutants thereof. From 1 to about 4 amino acids can be substituted to make up the immunogenic fragments or mutants of peptide B7080, without essentially detracting from the immunological properties of peptide B7080. For example, as shown in Table 2, amino acid changes can be made at positions 3, 5 and/or 6 of the B7080 epitope sequence depicted by SEQ ID NO: 35. In this embodiment, the polypeptide can be selected from the group consisting of MVA189R, Copenhagen B22R(C16L), Bangladesh-1975 D2L, India-1967 D1L, Garcia-1966 B1L, GRI-90 D5L (I1R), Brighton Red CPXV009 (CPXV222) or Zaire-96-I-16 N1R or other homologues of vaccinia and variola virus. In another embodiment, the method can further comprise one or more additional polypeptides comprising a peptide selected from the group consisting of: 74A, 165, 029D, B7034 and immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide B7034, immunogenic fragments or mutants thereof. From 1 to about 4 amino acids can be substituted to make up the immunogenic fragments or mutants of peptide B7034, without essentially detracting from the immunological properties of peptide B7034. For example, as shown in Table 2, amino acid changes can be made at position 3 of the B7034 epitope sequence depicted by SEQ ID NO: 36. In this embodiment, the polypeptide can be selected from the group consisting of MVA090R, Copenhagen J6R, Bangladesh-1975 L6R, India-1967 L6R, Garcia-1966 M6R, GRI-90 O4R, Brighton Red CPXV109 or Zaire-96-I-16 L6R or other homologues of vaccinia and variola virus. In another embodiment, the method can further comprise one or more additional polypeptides comprising a peptide selected from the group consisting of: 74A, 165, 029D, B7080 and immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

Several methods are described in the literature which are useful for the identification of T cell epitopes. For example, DeLisi et al. have suggested that potential epitopes may be located by identification of potential amphipathic alpha helical regions in the molecule. DeLisi et al., *Proc. Natl. Acad.*

Sci. USA 82:7048 (1987). Bixler et al. describe a strategy of synthesizing overlapping synthetic peptides encompassing an entire protein molecule for delineation of T cell epitopes. Bixler et al., *Immunol. Com.* 12:593 (1983); Bixler et al. *J. Immunogenet.* 11:339 (1994). A synthetic method described by Gysen (*Ciba Foundation Symposium* 119:130 (1986)) permits synthesis of a large variety of peptides thereby mimicking of a variety of potential binding sites, in turn allowing rapid scanning of a molecule.

More traditional methods, such as enzymatic or chemical digestion of proteins provide peptide fragments which may be tested for T cell activity. For example, enzymes such as chymotrypsin, elastase, ficin, papain, pepsin, or trypsin provide limited and predictable fragments by cleavage of specified amino acid linkages; similarly chemical compounds such as N-chloro-succinimide BPNS-skatole, cyanogen bromide, formic acid, or hydroxylamine, also produce definable fragments by their action on proteins. The presence of the desired T cell stimulating activity in any given fragment can be determined by subjecting purified fragments to a standard T cell proliferation assay, or by analyzing unpurified fragments with a T cell Western Assay. Young et al., *Immunol.* 59:167 (1986).

Peptide 74A, peptide 165, peptide 029D, peptide B7080 and peptide B7034 of the invention are CD8 epitopes and the T cells specific for these peptides are $CD8^+$ T cells. The effector functions of $CD8^+$ T cells include lysis of antigen presenting cells and release of cytokines. Therefore, the extent of $CD8^+$ T cell response to the antigen presenting cells can be determined using an assay for cell lysis or by measuring the production of one or more cytokines. The $CD8^+$ T cell response can also be measured by measuring the extent of release of one or more cytokines. In general, greater cell lysis activity or cytokine release will correlate with greater immunogenicity.

In one embodiment, the present invention relates to methods for immunizing an individual, particularly a human, against infection by vaccinia and/or variola virus by inducing an immune response against a polypeptide comprising peptide 74A, peptide 165, peptide 029D, peptide B7080, peptide B7034 or combinations thereof. In a further embodiment, the immune response can be induced against a polypeptide comprising an immunogenic fragment or mutant of peptide 74A, peptide 165, peptide 029D, peptide B7080, peptide B7034 or combinations thereof. Although the methods described herein are particularly useful for human immunization, the methods are equally applicable to other mammals (e.g., primate, canine, bovine, feline, rodent). In particular embodiments, the individual is positive for the HLA-A0201 gene. In other embodiments, the individual is positive for the HLA-B7 gene.

In another embodiment, the invention encompasses a method for inducing an immune response against vaccinia and/or variola virus in an individual, comprising administering to the individual a composition comprising one or more isolated polypeptides that comprise a peptide selected from the group consisting of peptide 74A, peptide 165, peptide 029D, peptide B7080, peptide B7034, variants thereof, immunogenic fragments thereof and mutants thereof, and optionally an adjuvant, whereby an immune response is induced against vaccinia and/or variola virus in the individual. In a particular embodiment, the composition consists essentially of one or more isolated polypeptides that comprise a peptide selected from the group consisting of peptide 74A, peptide 165, peptide 029D, peptide B7080, peptide B7034, variants thereof, immunogenic fragments thereof and mutants thereof, and optionally an adjuvant. In another embodiment, the composition consists of one or more isolated polypeptides that comprise a peptide selected from the group consisting of peptide 74A, peptide 165, peptide 029D, peptide B7080, peptide B7034, variants thereof, immunogenic fragments thereof and mutants thereof, and optionally an adjuvant. In another embodiment, one or more peptides selected from the group consisting of peptide 74A, peptide 165, peptide 029D, peptide B7080, variants thereof, immunogenic fragments thereof and mutants thereof, and optionally an adjuvant, are present in the composition. In a particular embodiment, at least one of the peptides described herein, (e.g., peptide B7034) is not present in the composition. In yet another embodiment, the composition does not include a whole organism (e.g., virus) of a vaccinia virus, a variola virus or other related poxvirus, as the invention provides for vaccines which do not comprise whole virus, attenuated virus or substantial portions thereof.

As used herein, an adjuvant refers to any chemical substance that induces or enhances antibody production and/or the immune response to a vaccine in a living organism. An example of a particularly suitable adjuvant for use in the methods of the invention is alum (aluminum hydroxide and/or aluminum phosphate). Examples of other adjuvants include, but are not limited to oil/surfactant based adjuvants (e.g., complete and incomplete Freund's emulsified oil adjuvants, Montanide ISA adjuvants, Ribi's adjuvants, Hunter's TiterMax, Arlacel A, mineral oil, emulsified peanut oil adjuvant (adjuvant 65)), mineral compounds (e.g., calcium phosphate, mineral salts of cerium, calcium and aluminum), bacterial products (e.g., lipopolysaccharide, cholera toxin, *Bordetella pertussis*), immunostaining complexes (IS-COMs), nitrocellulose-adsorbed protein, Gerbu adjuvant and organic polymers (e.g., squalene).

In one embodiment, the isolated polypeptide comprises peptide 74A (e.g., SEQ ID NO: 1). In a particular embodiment, the peptide 74A can be derived from a viral protein (e.g., MVA189R, Copenhagen B22R, Copenhagen C16L, Bangladesh-1975 D2L, India-1967 D1L, Garcia-1966 B1L, Brighton Red V212, Zaire-96-I-16 N1R). In another embodiment, the isolated polypeptide comprises peptide 165 (e.g., SEQ ID NO: 2, SEQ ID NO: 3). In a certain embodiment, the peptide 165 can be derived from a viral protein (e.g., MVA018L, Copenhagen C7L, Tian Tan TC7L, Bangladesh-1975 D11L, India-1967 D8L, Garcia-1966 B14L, Brighton Red V028, Zaire-96-I-16 D10L). In a further embodiment, the isolated polypeptide comprises peptide 029D (e.g., SEQ ID NO: 34, SEQ ID NO: 37, SEQ ID NO: 38, SEQ ID NO: 39). In a particular embodiment, the peptide 029D can be derived from a viral protein (e.g., MVA160L, Copenhagen A47L, Bangladesh-1975 J1L, India-1967 J1L, Garcia-1966 K1L, GRI-90 A50L, Brighton Red CPXV185). In yet another embodiment, the isolated polypeptide comprises peptide B7080 (e.g., SEQ ID NO: 35, SEQ ID NO: 40, SEQ ID NO: 41). In a certain embodiment, the peptide B7080 can be derived from a viral protein (e.g., MVA189R, Copenhagen B22R(C16L), Bangladesh-1975 D2L, India-1967 D1L, Garcia-1966 B1L, GRI-90 D5L (I1R), Brighton Red CPXV009 (CPXV222), Zaire-96-I-16 N1R). In yet an additional embodiment, the isolated polypeptide comprises peptide B7034 (e.g., SEQ ID NO: 36, SEQ ID NO: 42). In a certain embodiment, the peptide B7034 can be derived from a viral protein (e.g., MVA090R, Copenhagen J6R, Bangladesh-1975 L6R, India-1967 L6R, Garcia-1966 M6R, GRI-90 O4R, Brighton Red CPXV109, Zaire-96-I-16 L6R).

As used herein the terms "immunogenic fragment" and "mutant" of peptide 74A, peptide 165, peptide 029D, peptide B7080 and/or peptide B7034 refer to polypeptides in which 1 to about 4 amino acids have been substituted without essentially detracting from the immunological properties thereof can be generated in a variety of ways. For example, in vitro mutagenic techniques can be used to modify the cloned gene encoding peptide 74A, peptide 165, peptide 029D, peptide B7080 and/or peptide B7034. Such methods, which are well known to one skilled in the art, can be used to delete, insert or substitute nucleotides in the gene resulting in the deletion, insertion or substitution of amino acids in the encoded product. Examples of immunogenic fragments or mutants of peptide 74A and peptide 165 include, but are not limited to, those shown in Table 4. The immunological properties of the mutagenized encoded product can be assayed using methods such as those which are well known to one skilled in the art.

TABLE 4

Examples of immunogenic fragments and mutants of peptide 74A and peptide 165.

| Possible Immunogenic fragments or mutants | 74A peptide | 165 peptide |
|---|---|---|
| 1  | ILTEYILWV (SEQ ID NO: 4)  | IVDDTFYYV (SEQ ID NO: 19) |
| 2  | LLTEYILWV (SEQ ID NO: 5)  | LVDDTFYYV (SEQ ID NO: 20) |
| 3  | FLTEYILWV (SEQ ID NO: 6)  | FVDDTFYYV (SEQ ID NO: 21) |
| 4  | CLAEYILWV (SEQ ID NO: 7)  | KVADTFYYV (SEQ ID NO: 22) |
| 5  | CLYEYILWV (SEQ ID NO: 8)  | KVYDTFYYV (SEQ ID NO: 23) |
| 6  | CLFEYILWV (SEQ ID NO: 9)  | KVFDTFYYV (SEQ ID NO: 24) |
| 7  | CLTEIILWV (SEQ ID NO: 10) | KVDDIFYYV (SEQ ID NO: 25) |
| 8  | CLTEKILWV (SEQ ID NO: 11) | KVDDKFYYV (SEQ ID NO: 26) |
| 9  | CLTENILWV (SEQ ID NO: 12) | KVDDYFYYV (SEQ ID NO: 27) |
| 10 | CLTEYIAWV (SEQ ID NO: 13) | KVDDTFAYV (SEQ ID NO: 28) |
| 11 | CLTEYIYWV (SEQ ID NO: 14) | KVDDTFHYV (SEQ ID NO: 29) |
| 12 | CLTEYIHWV (SEQ ID NO: 15) | IVADTFYYV (SEQ ID NO: 30) |
| 13 | ILAEYILWV (SEQ ID NO: 16) | IVADIFYYV (SEQ ID NO: 31) |
| 14 | ILAEIILWV (SEQ ID NO: 17) | IVADIFAYV (SEQ ID NO: 32) |
| 15 | ILAEIIAWV (SEQ ID NO: 18) | LVYDKFHYV (SEQ ID NO: 33) |

Effective dosages for inducing an immune response (e.g., a virus protective response) against vaccinia and/or variola can be determined empirically with initial dosage ranges based upon historical data for peptide/protein vaccine compositions. As used herein, the terms "induced immune response" or "virus protective response" refers to an immunological response in the individual resulting in the successful control or limitation of infection by vaccinia and/or variola virus which is clinically observed.

For example, individuals can be administered dosages of peptide 74A, peptide 165, peptide 029D, peptide B7080 and/or peptide B7034 ranging from 0.5-500 micrograms. Whether a particular dosage is effective can be determined using well known T cell proliferation and cytotoxicity assays. For example, following administration of the protein to an individual blood is drawn. Cytotoxic T cells are identifiable by $^{51}$Cr release assay (see e.g., Kuwano et al., *J. Virol.* 140: 1264-1268 (1988)). Helper T cells are identifiable by a standard T cell proliferation assay (see e.g., Kurane et al., *J. Clin. Invest.* 83:506-513 (1989)). The results from these studies are compared with results from the same experiments conducted with T cells from the same individual prior to administration of the antigen. By comparing this data, effective dosage ranges can be determined.

A wide variety of pharmaceutically acceptable carriers are useful. Pharmaceutically acceptable carriers include, for example, water, physiological saline, ethanol polyols (e.g., glycerol or administration is typically parenteral (i.e., intravenous, intramuscular, intraperitoneal or subcutaneous). An adjuvant (e.g., alum, others described herein) can also be included in the vaccine mixture.

The invention also pertains to a method for immunizing an individual against infection by vaccinia and/or variola virus by administering a vaccine composition comprising at least one essentially pure T cell epitope (e.g., peptide 74A, peptide 165, peptide 029D, peptide B7080, peptide B7034) in combination with a pharmaceutically acceptable carrier. Due to genetic variability between individuals, a single T cell epitope may not stimulate a virus protective response in all individuals to whom it is administered. Therefore, by combining two or more distinct T cell epitopes (e.g., of peptide 74A, peptide 165, peptide 029D, peptide B7080 and/or peptide B7034), the vaccine is more broadly effective. As indicated above, helper T cell epitopes and cytotoxic T cell epitopes are thought to comprise distinct (albeit possibly overlapping) regions of proteins. Cytotoxic T cell epitopes can be distinguished from helper T cells epitopes experimentally using the cytoxicity and proliferation assays described above (helper T cells stimulate proliferation but do not posses cytotoxic activity).

All or an immunogenic fragment or mutant of peptide 74A, peptide 165, peptide 029D, peptide B7080 and/or B7034 can be administered as a polypeptide. Such polypeptides can be synthesized chemically. Alternatively, all, a truncated portion of (e.g., immunogenic fragment), or a mutant of a gene encoding peptide 74A, peptide 165, peptide 029D, peptide B7080 and/or peptide B7034 can be expressed in a cell, and the encoded product can be isolated using known methods (e.g., column chromatography, gel electrophoresis, etc.).

As used herein, the term polypeptide means any amino acid sequence which is identical or has substantial sequence homology or identity to peptide 74A, peptide 165, peptide 029D, peptide B7080 and/or peptide B7034. The expression "substantial homology or identity" refers to polypeptides having an amino acid sequence in which amino acids of peptide 74A, peptide 165, peptide 029D, peptide B7080 or peptide B7034 have been substituted without essentially detracting from the immunological properties thereof. This definition includes amino acid sequences of sufficient length to be classified as oligopeptides (these terms are not used consistently or with great precision in the literature).

In one embodiment, both a helper T cell epitope and a cytotoxic T cell epitope can be administered to the individual. The stimulation of cytotoxic T cells is desirable in that these cells will kill cells infected by vaccinia and/or variola virus. The stimulation of helper T cells is beneficial in that they secrete soluble factors which have a stimulatory effect on other T cells, as well as B cells.

Identification of these epitopes will enable the analysis and quantitation of vaccinia virus-specific $CD8^+$ T cells in the acute and memory phases and to compare $CD8^+$ T cell responses specific to different epitopes. Additionally, expansion and subsequent shrinkage of epitope-specific $CD8^+$ T cells at the T cell receptor level can be monitored. Definition of T cell epitopes will help us to better understand human T cell responses to vaccinia virus as a model of human infection. In addition, it will provide a quantitative measure of poxvirus T cell immunity when these viruses are used as viral vectors.

In another embodiment, the invention provides a method for inducing an immune response against vaccinia and/or variola virus in an individual, comprising administering to the individual a composition comprising one or more isolated nucleic acid molecules, wherein the one or more isolated nucleic acid molecules encodes a polypeptide that comprises a peptide selected from the group consisting of peptide 74A, peptide 165, peptide 029D, peptide B7080, peptide B7034, variants thereof, immunogenic fragments thereof and mutants thereof, and optionally, an adjuvant, whereby an immune response is induced against vaccinia and/or variola virus in the individual. In a particular embodiment, the nucleic acid is in a vector. In a certain embodiment, the composition consists essentially of one or more isolated nucleic acid molecules, wherein the one or more isolated nucleic acid molecules encodes a polypeptide that comprises a peptide selected from the group consisting of peptide 74A, peptide 165, peptide 029D, peptide B7080, peptide B7034, variants thereof, immunogenic fragments thereof and mutants thereof, and, optionally, an adjuvant. In yet another embodiment, the composition consists of one or more isolated nucleic acid molecules, wherein the one or more isolated nucleic acid molecules encodes a polypeptide that comprises a peptide selected from the group consisting of peptide 74A, peptide 165, peptide 029D, peptide B7080, peptide B7034, variants thereof, immunogenic fragments thereof and mutants thereof, and, optionally, an adjuvant.

As used herein, the term "nucleic acid" refers to polynucleotides, such as deoxyribonucleic acid (DNA), and ribonucleic acid (RNA). The term should also be understood to include analogs of either RNA or DNA that are made from nucleotide analogs. The nucleic acids described herein can also be single (sense or antisense) or double-stranded polynucleotides. The nucleic acids for use in the present invention may include unconventional modifications to any portion, including, for example, the sugar phosphate backbone or the base portion of one or more nucleotides. Furthermore, the nucleic acids for use in the present invention may be naturally-occurring, recombinant or synthetic.

In one embodiment, the isolated nucleic acid molecule encodes a polypeptide comprising peptide 74A (SEQ ID NO: 1). In another embodiment, the isolated nucleic acid molecule encodes a polypeptide comprising peptide 165 (e.g., SEQ ID NO: 2, SEQ ID NO: 3). In yet another embodiment, the isolated nucleic acid molecule encodes a polypeptide comprising peptide 029D (e.g., SEQ ID NO: 34, SEQ ID NO: 37, SEQ ID NO: 38, SEQ ID NO: 39). In an additional embodiment, the isolated nucleic acid molecule encodes a polypeptide comprising peptide B7080 (e.g., SEQ ID NO: 35, SEQ ID NO: 40, SEQ ID NO: 41). In a certain embodiment, the isolated nucleic acid molecule encodes a polypeptide comprising peptide B7034 (e.g., SEQ ID NO: 36, SEQ ID NO: 42).

In a particular embodiment, a nucleic acid encoding a polypeptide that comprises a peptide selected from the group consisting of peptide 74A, peptide 165, peptide 029D, peptide B7080, peptide B7034, variants thereof, immunogenic fragments thereof and mutants thereof, is provided to an intended host (e.g., a cell, a subject) as an expression vector. As used herein, an "expression vector" is a vector that comprises an isolated nucleic acid and can be used to deliver the isolated nucleic acid to the interior of a cell, such that a gene product encoded by or specified by the isolated nucleic acid is expressed or generated in the cell. Numerous expression vectors are known in the art including, but not limited to, linear polynucleotides, polynucleotides associated with ionic or amphiphilic compounds, plasmids, and viruses. Expression vectors generally comprise a promoter that is operably-linked with a portion of the isolated nucleic acid that encodes or specifies a gene product.

One of skill in the art could readily identify and insert a nucleic acid encoding a polypeptide that comprises a peptide selected from the group consisting of peptide 74A, peptide 165, peptide 029D, peptide B7080, peptide B7034, variants thereof, immunogenic fragments thereof and mutants thereof, into an appropriate expression vector using standard techniques and readily available starting materials (e.g., a plasmid, phage, viral particle or other vector, which, when introduced into an appropriate host, contains the necessary genetic elements to direct expression of the sequence that encodes the polypeptide). This coding sequence is operably-linked to necessary regulatory sequences. Several expression vectors are well known and are commercially available. For example, one having ordinary skill in the art can, using well known techniques and readily available starting materials, insert a DNA molecule into a commercially available expression vector. Expression systems containing the requisite control sequences, such as promoters and polyadenylation signals, and preferably enhancers, are readily available and known in the art for a variety of hosts (see e.g., Sambrook, et al., Molecular Cloning a Laboratory Manual, Second Ed. Cold Spring Harbor Press (1989)).

A nucleic acid encoding a polypeptide that comprises a peptide selected from the group consisting of peptide 74A, peptide 165, peptide 029D, peptide B7080, peptide B7034, variants thereof, immunogenic fragments thereof and mutants thereof, may be provided to (e.g., introduced into) a cell or administered to a subject under conditions in which the active polypeptide is expressed in vitro or in vivo. For this purpose, various techniques and reagents have been developed. For example, a number of viral vectors have been developed that allow for transfection and, in some cases, integration of the virus into the host (e.g., cell or subject). See, for example, Dubensky et al. (1984) *Proc. Natl. Acad. Sci. USA* 81, 7529-7533; Kaneda et al. (1989) *Science* 243, 375-378; Hiebert et al. (1989) *Proc. Natl. Acad. Sci. USA* 86, 3594-3598; Hatzoglu et al. (1990) *J. Biol. Chem.* 265, 17285-17293 and Ferry, et al. (1991) *Proc. Natl. Acad. Sci. USA* 88, 8377-8381. The vector may be administered by injection, e.g. intravascularly or intramuscularly, inhalation, or another parenteral mode. Non-viral delivery methods such as administration of the DNA via complexes with liposomes, or by injection, catheter or biolistics, may also be used.

Any means for introducing polynucleotides into cells or mammals (human or non-human) may be adapted to the practice of this invention for the delivery of the various nucleic acid constructs into the intended recipient (e.g., a host cell or a host subject). Gene transfer methodologies can be employed to transfer a coding sequence for a polypeptide that comprises a peptide selected from the group consisting of peptide 74A, peptide 165, peptide 029D, peptide B7080, peptide B7034, variants thereof, immunogenic fragments thereof and mutants thereof, to a subject such that the gene can be replicated and expressed in vivo. Particularly useful gene therapy methods are discussed in the published international application WO 93/00051, which is incorporated herein by reference.

A gene or other nucleic acid (e.g., RNA, cDNA) encoding a peptide listed in Table 1 or Table 2, or a portion thereof (e.g., an immunogenic fragment), which comprises peptide 74A, peptide 165, peptide 029D, peptide B7080, or peptide B7034 can be cloned into a vector (e.g., a recombinant virus, an expression vector), which expresses peptide 74A, peptide 165, peptide 029D, peptide B7080, and/or peptide B7034, or an immunogenic fragment or mutant thereof, in the individual to be immunized. An example of such vector is the recombinant vaccinia virus system described by Paoletti et al. (U.S. Pat. No. 4,603,112), the disclosure of which is incorporated herein by reference. Other viruses have been described in the literature which have a genome that can accommodate the insertion of a foreign DNA such that a protein encoded by the DNA is expressed in vivo. Any such recombinant virus is useful for the practice of this invention. Examples of other suitable viral vectors include, but are not limited to, any of a variety of viral vectors useful in gene therapy (e.g., recombinant retroviruses (e.g., lentivirus), adenovirus, adeno-associated virus (AAV), herpes simplex derived vectors, hybrid adeno-associated/herpes simplex viral vectors, influenza viral vectors, especially those based on the influenza A virus, alphaviruses, for example the Sinbis and semliki forest viruses).

The present invention also relates to a method of identifying the presence of all, or an immunogenic portion of, a vaccinia, a variola virus and/or other related poxvirus in a sample comprising determining whether T cells present in the sample become activated in the presence of one or more peptides selected from the group consisting of: peptide 74A (SEQ ID NO: 1), peptide 165 (SEQ ID NO: 2), peptide 029D (SEQ ID NO: 34), peptide B7080 (SEQ ID NO: 35), peptide B7034 (SEQ ID NO: 36), an immunogenic mutant and fragment thereof, thereby producing a combination. The combination is maintained under conditions in which the T cells can become activated in the presence of the one or more peptides, wherein if the T cells become activated, all or an immunogenic portion of a vaccinia, a variola, and/or a related poxvirus is present in the sample. In one embodiment, the T cells are cytotoxic T lymphocytes (CTLs). In a particular embodiment, the T cells are CD8+ T cells. The T cells in the sample can also include other T cells (e.g., CD4+ T cells).

In another embodiment, the invention provides a method of identifying the presence of all, or an immunogenic portion of, a vaccinia, a variola virus and/or other related poxvirus in a sample, comprising contacting the sample with T cells that become activated in the presence of one or more peptides selected from the group consisting of: peptide 74A, peptide 165, peptide 029D, peptide B7080, peptide B7034, a mutant thereof and an immunogenic fragment thereof, thereby producing a combination. The combination is maintained under conditions in which the T cells can become activated in the presence of the one or more peptides, wherein if the T cells become activated, then all, or an immunogenic portion of, a vaccinia, a variola, and/or a related poxvirus is present in the sample.

In yet another embodiment, the invention is directed to a method of identifying whether T cells present in a sample have been contacted (e.g., previously contacted) with all or an immunogenic portion of a vaccinia, a variola and/or a related poxvirus, comprising contacting the T cells with one or more peptides selected from the group consisting of: peptide 74A, peptide 165, peptide 029D, peptide B7080, peptide B7034, a mutant thereof and an immunogenic fragment thereof, thereby producing a combination. The combination is maintained under conditions in which the T cells can become activated in the presence of the one or more peptides, wherein if the T cells become activated, then the T cells have been contacted with all or an immunogenic portion of a vaccinia, a variola, and/or a related poxvirus.

As used herein a "sample" for use in the methods of the present invention can be any type of sample that can be analyzed in the method and can be obtained from a variety of sources. The sample can comprise all (e.g., a whole virus), or an immunogenic portion of, a vaccinia, a variola, and/or a related poxvirus. As used herein, an "immunogenic portion of a vaccinia, a variola, and/or a related poxvirus" refers to a portion of the organism of sufficient size to elicit an immune response in an individual. In a particular embodiment, an "immunogenic portion of a vaccinia, a variola, and/or a related poxvirus" is of a sufficient size to activate T cells (e.g. activate T cells previously exposed to or contacted with a vaccinia, a variola, and/or a related poxvirus). Alternatively, or in addition, T cells can be present in the original sample or can be added to the sample. In a particular embodiment, the T cells have been previously exposed to all, or an immunogenic portion of, a vaccinia, a variola, and/or a related poxvirus. The sample can be one which is found in any environment, such as a powder, or a liquid. In addition, the sample can be obtained from a host, such as a mammalian host or individual (e.g., human, equine, canine, feline, bovine, murine). Samples from a host include blood (e.g., whole blood, PMBCs), lymph (e.g. lymph fluid) and tissue (e.g., lymph nodes, spleen). In a particular embodiment, the sample is from an individual that is positive for the HLA-A0201 gene. In another embodiment, the sample is from an individual that is positive for the HLA-B7 gene.

For example, the sample can be a sample which does not initially contain T cells. In this embodiment, the sample is contacted with T cells that become activated in the presence of a vaccinia, variola and/or other related poxvirus. Then whether the T cells become activated in the presence of the polypeptide is determined, wherein if the T cells become activated, then vaccinia, variola and/or other related poxvirus is present in the sample. In another embodiment, the sample can be blood which contains T cells. In this embodiment, whether the T cells become activated in the presence of the polypeptide is determined, wherein if the T cells become activated, then vaccinia, variola and/or other related poxvirus is present in the sample.

Thus, the present invention also relates to a method of determining whether an individual has been infected with vaccinia, variola virus and/or other related pox virus comprising determining whether the individual's T cells become activated in the presence of polypeptide selected from the group consisting of peptide 74A (SEQ ID NO: 1), peptide 165 (SEQ ID NO: 2), peptide 029D (SEQ ID NO: 34), peptide B7080 (SEQ ID NO: 35), peptide B7034 (SEQ ID NO: 36), an immunogenic mutant or fragment thereof and a combination thereof, and wherein if the individual's T cells become activated in the presence of the peptide, then the individual has been infected with vaccinia, variola and/or other related poxvirus.

As described herein, peripheral T cells in the blood and organs of the immune system (e.g. spleen and lymph nodes) exist in a quiescent or resting state. Upon interaction of T cells with an MHC/epitope complex, the T cells proliferate and differentiate into activated cells having a variety of functions. $CD8^+$ T cells typically become cytotoxic upon activation and destroy antigen-presenting cells via direct contact. Activated $CD4^+$ T cells provide a helper function to B cells, enabling B cells to differentiate into antibody-producing cells. Activated $CD8^+$ T cells and $CD4^+$ T cells release a variety of cytokines (lymphokines or interleukins), which can, for example, control differentiation of many classes of lymphocytic precursor cells.

As used herein, the phrase "T cells become activated" refers to activation of T cells upon recognition of a specific antigen (e.g., peptide 74A (SEQ ID NO: 1), peptide 165 (SEQ ID NO: 2), peptide 029D (SEQ ID NO: 34), peptide B7080 (SEQ ID NO: 35), peptide B7034 (SEQ ID NO: 36), an immunogenic mutant or fragment thereof and/or a combination thereof). Characteristics of activated T cells are well known to those of skill in the art. For example, activated T cells can be evidenced by secretion of autocrine growth factors (e.g., IL-2, IL-4), proliferation of (e.g., clonal expansion) and/or differentiation of antigen-specific T cells, among others.

Whether the T cells present in the sample become activated can be determined using a variety of assays known to those of skill in the art. For example, a cytokine assay (e.g., ELISPOT), a flow cytometry assay (e.g., tetramer staining assay), intracellular cytokine staining assay (ICS) and/or a limiting dilution assay (LDA) can be used in the methods of the present invention.

Poxviruses such as vaccinia virus allow for simplified integration of multiple foreign genes with high levels of expression, and thus, are widely used for the cytoplasmic expression of recombinant genes in mammalian cells. Vaccinia virus mutants and other poxviruses are receiving special attention because of their diminished cytopathic effects and increased safety. For example, replicating and non-replicating vectors encoding the bacteriophage T7 RNA polymerase for transcription of recombinant genes and numerous cancer antigens have been engineered (Carroll, M. W. and Moss B., *Curr. Opin. Biotechnol.*, 8(5):573-577 (1997); Carroll, M. W., et al., *Vaccine*, 15(4):387-394 (1997).

The invention also relates to a method of monitoring the effectiveness of a vaccinia, variola and/or other related pox virus vaccine in an individual who has been administered the vaccinia vaccine. The method comprises determining whether the individual's T cells become activated in the presence of a polypeptide selected from the group consisting of: peptide 74A (SEQ ID NO: 1), peptide 165 (SEQ ID NO: 2), peptide 029D (SEQ ID NO: 34), peptide B7080 (SEQ ID NO: 35), peptide B7034 (SEQ ID NO:36), an immunogenic mutant or fragment thereof and a combination thereof, wherein if the individual's T cells become activated, then the virus is effective in the individual. In one embodiment, the vaccine is a vaccinia vaccine. In another embodiment, the vaccine is vaccinia virus that is a cancer vaccine.

Exemplification

Donors

Donors in this study were three HLA-A0201-positive laboratory workers received primary immunization by scarification with the licensed smallpox vaccine, Dryvax®, as recommended by the Centers for Disease Control and Prevention for laboratory personnel working with vaccinia viruses. The HLA-A and B alleles of donor 1 were A2 (A0201), B15, B18; those of donor 2 were A2 (A0201), B15, B44; and those of donor 3 were A2 (A0201), A31, B40, B51.

Viruses

Vaccinia virus New York City Board of Health (NYCBH), the same strain used to produce Dryvax®, was provided by Gail Mazzara and Dennis Panicali of Applied Biotechnology, Inc, and propagated and titrated in CV-1 cells (ATCC # CCL-70) as previously described (Littuau, R. A., et al., *J. Virol.*, 66:2274-2280 (1992); Terajima, M. et al., *Virus Res.* 84:67-77 (2002)). Modified vaccinia virus Ankara strain (MVA) was kindly supplied by Bernard Moss of National Institute of Allergy and Infectious Diseases/National Institute of Health, and was propagated and titrated in BHK-21 cells (ATCC # CCL-10) following published methods (Carroll, M. W., et al., *Virology* 238:198-211 (1997)).

CTL Lines

Vaccinia virus-specific CTL lines were isolated from peripheral blood mononuclear cells (PBMCs) of immunized donors by limiting dilution cloning (Demkowicz, W. E., et al., *J. Virol.* 67:1538-1544 (1993)). Vaccinia virus NYCBH strain was used to stimulate PBMCs for cloning and to infect target cells for cytotoxicity assays. Cytotoxicity assays were performed as previously described (Frey, S. E., et al., *J. Med.* 346:1275-1280 (2002)). Hmy C1R A2.1 cells (gift from William E. Biddison of NIH/NINDS), which express only HLA-A0201 at normal levels, were used as targets in cytotoxicity assay to confirm the HLA-A0201 restriction. Surface expression of CD4 and CD8 was determined by flow cytometry using FITC-conjugated antibodies (Becton Dickinson). Cross-reactivity of CTL lines was determined using autologous B-LCLs (B-lymphoblastoid cell lines), that were infected with MVA as target cells in cytotoxicity assays.

Screening Peptides in Cytotoxicity Assay

Peptides were synthesized with a Symphony automated peptide synthesizer at the Protein Core Facility in the University of Massachusetts Medical School or purchased from Mimotopes Pty. Ltd. When predicted epitopes overlapped, we made them as a longer peptide fragment. For technical reasons some of these screening peptides were made as a 13mer instead of a 9mer. In screening cytotoxicity assays, mixtures of five peptides were used and the concentration of each peptide was 5 mg/ml. When the peptide recognized was longer than 9 amino acids, truncated 9mer peptide epitopes were constructed and analyzed in cytotoxicity assays. All peptides recognized were tested in dose-response experiments (FIG. 1).

Tetramer Staining

Peptide/HLA-A0201 tetramers were made in the Tetramer Core Facility in the University of Massachusetts Medical School following the protocol published previously (Catalina, M. D., et al., *J. Immunol.*, 167:4450-4457 (2001)). Each lot of tetramer was titrated using CTL lines specific to the peptide mixed with autologous PBMCs at a 1 to 10 (or 20) ratio to determine the optimal concentration for staining.

Interferon (IFN)-γ ELISPOT Assays

IFN-γ ELISPOT assays were performed as previously described (Ennis, F., et al., *J. Infect. Dis.* 185:1657-1659 (2002)). For stimulation, PBMCs were incubated with vaccinia virus NYCBH strain at an MOI of 1 or with peptide at a final concentration of 4 µg/ml for 16 hours in triplicate wells. Responses in day 45 samples were considered positive if a minimum of five IFN-γ producing cells were present in the well and if the number of IFN-γ producing cells was at least twice that of the day 0 sample. The number of spots in the day 0 samples was subtracted from the number of spots in the day 45 samples, and T cell frequency was calculated as the number of IFN-γ producing cells/$10^6$ PBMCs (Van Epps H. L., et al., *J. Exp. Med.* 196:579-588 (2002)).

While this invention has been particularly shown and described with references to particular embodiments thereof, it will be understood by those skilled in the art that various changes in form and details may be made therein without departing from the scope of the invention encompassed by the appended claims.

What is claimed is:

1. A method for inducing a T cell immune response against a vaccinia and/or variola virus antigen in an individual, wherein said vaccinia and/or variola virus antigen comprises a T cell epitope that is identical or has substantial homology to peptide B7080 (SEQ ID NO: 35), comprising administering to said individual a composition consisting essentially of one or more isolated peptides selected from the group consisting of: peptide B7080 (SEQ ID NO: 35) and one or more homologues of peptide B7080, and, optionally an adjuvant, wherein 1 to 4 amino acids of SEQ ID NO: 35 are substituted in the one or more homologues of peptide B7080, and the one or more homologues of peptide B7080 are the same length as SEQ ID NO: 35 and maintain the function of SEQ ID NO: 35 as a CD8 T cell epitope of the vaccinia or variola virus; whereby a T cell immune response is induced against the vaccinia and/or variola virus antigen in said individual.

2. The method of claim 1, wherein the peptide is isolated from a protein selected from the group consisting of: MVA189R, Copenhagen B22R(C16L), Bangladesh-1975 D2L, India-1967 D1L, Garcia-1966 B1L, GRI-90 D5L (I1R), Brighton Red CPXV009 (CPXV222) and Zaire-96-I-16 N1R.

3. The method of claim 1, wherein the adjuvant is alum.

4. A method of identifying T cells in a sample that become activated in the presence of a vaccinia and/or a variola virus, wherein said vaccinia and/or variola virus comprises a polypeptide having an amino acid sequence that is identical or has substantial homology to peptide B7080 (SEQ ID NO: 35), comprising contacting the T cells with one or more peptides selected from the group consisting of: peptide B7080 (SEQ ID NO: 35) and one or more homologues of peptide B7080, wherein 1 to 4 amino acids of SEQ ID NO: 35 are substituted in the one or more homologues of peptide B7080, and the one or more homologues of peptide B7080 are the same length as SEQ ID NO: 35 and maintain the function of SEQ ID NO: 35 as a CD8 T cell epitope of the vaccinia or variola virus, and wherein activation of the T cells by the one or more peptides indicates that the T cells become activated in the presence of the vaccinia and/or variola virus.

5. The method of claim 4 wherein whether the T cells become activated is determined using an assay selected from the group consisting of: a cytokine assay, a flow cytometry assay and a limiting dilution assay.

6. The method of claim 5 wherein the cytokine assay is an ELISPOT assay and the flow cytometry assay is a tetramer staining assay.

7. The method of claim 4 wherein the sample is selected from the group consisting of: blood, lymph and tissue.

8. The method of claim 4 wherein the sample comprises peripheral blood mononuclear cells.

9. A method of determining whether an individual has T cells that become activated in the presence of a vaccinia or variola virus, wherein said vaccinia or variola virus comprises a polypeptide having an amino acid sequence that is identical or has substantial homology to peptide B7080 (SEQ ID NO: 35), the method comprising determining whether T cells from said individual become activated in the presence of one or more peptides selected from the group consisting of: peptide B7080 (SEQ ID NO: 35) and one or more homologues of peptide B7080, wherein 1 to 4 amino acids of SEQ ID NO: 35 are substituted in the one or more homologues of peptide B7080, and the one or more homologues of peptide B7080 are the same length as SEQ ID NO: 35 and maintain the function of SEQ ID NO: 35 as a CD8 T cell epitope of the vaccinia or variola virus, and wherein activation of the T cells of said individual by said one or more peptides indicates the individual has T cells that become activated in the presence of the vaccinia or variola virus.

10. The method of claim 9 wherein the T cells from said individual are present in a sample, and the sample is selected from the group consisting of: blood, lymph and tissue.

11. The method of claim 9 wherein the sample comprises peripheral blood mononuclear cells.

12. The method of claim 9 wherein whether the T cells of said individual become activated is determined using an assay selected from the group consisting of: a cytokine assay, a flow cytometry assay and a limiting dilution assay.

13. The method of claim 12 wherein the cytokine assay is an ELISPOT assay and the flow cytometry assay is a tetramer staining assay.

14. A method of monitoring the effectiveness of a vaccinia and/or variola vaccine in an individual who has been administered said vaccine, comprising determining whether T cells of said individual become activated in the presence of one or more peptides selected from the group consisting of: peptide B7080 (SEQ ID NO: 35) and one or more homologues of peptide B7080, wherein 1 to 4 amino acids of SEQ ID NO: 35 are substituted in the one or more homologues of peptide B7080, and the one or more homologues of peptide B7080 are the same length as SEQ ID NO: 35 and maintain the function of SEQ ID NO: 35 as a CD8 T cell epitope of the vaccinia or variola virus, and wherein if the individual's T cells become activated, then the vaccinia and/or variola vaccine is effective in the individual.

15. The method of claim 14 wherein the T cells of the individual are present in a sample, and the sample is selected from the group consisting of: blood, lymph and tissue.

16. The method of claim 14 wherein the sample comprises peripheral blood mononuclear cells.

17. The method of claim 14 wherein whether the T cells of the individual become activated is determined using an assay selected from the group consisting of: a cytokine assay, a flow cytometry assay and a limiting dilution assay.

18. The method of claim 17 wherein the cytokine assay is an ELISPOT assay and the flow cytometry assay is a tetramer staining assay.

19. The method of claim 14 wherein the vaccinia and/or variola vaccine is a cancer vaccine.

20. The method of claim 1, wherein the one or more homologues of peptide B7080 is SEQ ID NO:40 or SEQ ID NO:41.

21. The method of claim 4, wherein the one or more homologues of peptide B7080 is SEQ ID NO:40 or SEQ ID NO:41.

22. The method of claim 9, wherein the one or more homologues of peptide B7080 is SEQ ID NO:40 or SEQ ID NO:41.

23. The method of claim 14, wherein the one or more homologues of peptide B7080 is SEQ ID NO:40 or SEQ ID NO:41.

* * * * *

UNITED STATES PATENT AND TRADEMARK OFFICE
CERTIFICATE OF CORRECTION

| | | |
|---|---|---|
| PATENT NO. | : 8,067,535 B2 | |
| APPLICATION NO. | : 11/238122 | |
| DATED | : November 29, 2011 | |
| INVENTOR(S) | : Masanori Terajima, John Cruz and Francis A. Ennis | |

It is certified that error appears in the above-identified patent and that said Letters Patent is hereby corrected as shown below:

In Column 1 under Government Support:

Line 16, delete "supported, in whole or in party, by grants", insert --made with government support under Grant Nos.--;

Line 17, delete "AI-49320", insert --AI-049320--;

Line 17, delete "subcontracts", insert --subcontract--;

Line 17, delete "AI-46725", insert --AI-046725--;

Line 18, delete "and AI-46725";

Line 18, delete "from" and insert --awarded by--;

In Claim 1, Column 41:

Lines 24 through 25, delete "1 to 4 amino acids of SEQ ID NO: 35 are substituted in the one or more homologues of peptide B7080, and" and insert --the sequence of--;

Line 26, after "B7080", insert --is present in another vaccinia or variola virus, and the one or more homologues--;

Line 27, delete "maintain the" and "of SEQ ID NO: 35";

Line 28, before "CD8" delete "a";

Line 28, delete "epitope" and insert --epitopes--;

Signed and Sealed this
Sixth Day of March, 2012

David J. Kappos
*Director of the United States Patent and Trademark Office*

CERTIFICATE OF CORRECTION (continued)

U.S. Pat. No. 8,067,535 B2

In Claim 4, Column 41:

Line 43, after "comprising", insert --: 1)--;

Lines 46 through 47, delete "1 to 4 amino acids of SEQ ID NO: 35 are substituted in the one or more homologues of peptide B7080, and" and insert --the sequence of--;

Line 48, after "B7080", insert --is present in another vaccinia or variola virus, and the one or more homologues--;

Line 49, delete "maintain the" and "of SEQ ID NO: 35";

Line 50, before "CD8", delete "a";

Line 50, delete "epitope" and insert --epitopes--;

Line 50, delete "and" and insert --2) assaying for T cell activation in response to the one or more peptides, and 3) identifying T cells in the sample that are activated by the one or more peptides--;

In Claim 9, Column 42:

Lines 16 through 17, delete "determining whether T cells from said individual become activated in the presence of" and insert --: 1) contacting a sample containing T cells from the individual with--;

Lines 20 through 22, delete "1 to 4 amino acids of SEQ ID NO: 35 are substituted in the one or more homologues of peptide B7080, and" and insert --the sequence of--;

Line 22, before "are", insert --is present in another vaccinia or variola virus, and the one or more homologues--;

Line 23, delete "maintain the";

Line 24, delete "of SEQ ID NO: 35";

Line 24, before "CD8", delete "a";

Line 24, delete "epitope" and insert --epitopes--;

Line 25, delete "and" and insert --2) assaying for T cell activation in response to the one or more peptides, and 3) determining whether the T cells in the sample become activated in the presence of the one or more peptides--;

CERTIFICATE OF CORRECTION (continued)
U.S. Pat. No. 8,067,535 B2

In Claim 14, Column 42:

Line 42, after "vaccine", insert --in inducing a T cell immune response--;

Lines 43 through 44, delete "determining whether T cells of said individual become activated in the presence of" and insert --: 1) contacting a sample containing T cells from the individual with--;

Lines 48 through 50, delete "1 to 4 amino acids of SEQ ID NO: 35 are substituted in the one or more homologues of peptide B7080, and" and insert --the sequence of--;

Line 50, before "are", insert --is present in another vaccinia or variola virus, and the one or more homologues--;

Line 51, delete "maintain the";

Line 52, delete "of SEQ ID NO: 35";

Line 52, before "CD8", delete "a";

Line 53, delete "and" and insert --2) assaying for T cell activation in response to the one or more peptides, and 3) determining whether the T cells in the sample become activated in the presence of the one or more peptides--;

Line 54, after "effective", insert --in inducing a T cell immune response--.